United States Patent [19]

Gerecke et al.

[11] 4,346,031

[45] Aug. 24, 1982

[54] PROCESS FOR PREPARING IMIDAZODIAZEPINES

[75] Inventors: Max Gerecke; Willy Haefely, both of Reinach; Walter Hunkeler, Magden; Emilio Kyburz, Reinach, all of Switzerland; Hanns Möhler, Inzlingen, Fed. Rep. of Germany; Lorenzo Pieri, Riehen; Petar Polc, Binningen, both of Switzerland

[73] Assignee: Hoffmann-La Roche Inc., Nutley, N.J.

[21] Appl. No.: 321,492

[22] Filed: Nov. 16, 1981

Related U.S. Application Data

[62] Division of Ser. No. 193,775, Oct. 3, 1980, Pat. No. 4,316,839.

[30] Foreign Application Priority Data

| Oct. 4, 1979 [CH] | Switzerland | 8971/79 |
|---|---|---|
| Oct. 4, 1979 [CH] | Switzerland | 8972/79 |
| Nov. 30, 1979 [CH] | Switzerland | 10664/79 |
| Nov. 30, 1979 [CH] | Switzerland | 10665/79 |
| Jul. 25, 1980 [CH] | Switzerland | 5716/80 |

[51] Int. Cl.$^3$ .................. C07D 487/04; C07D 513/14
[52] U.S. Cl. ................. 260/239.3 T; 260/239.3 P; 260/239.3 B; 260/239.3 D
[58] Field of Search ............... 260/239.3 T, 239.3 B, 260/239.3 P

[56] References Cited

U.S. PATENT DOCUMENTS 4,316,839  2/1982  Gerecke et al. ............. 260/239.3 T

*Primary Examiner*—Robert T. Bond
*Attorney, Agent, or Firm*—Jon S. Saxe; Bernard S. Leon; Frank P. Hoffman

[57] ABSTRACT

Imidazodiazepine derivatives of the formula wherein A together with the two carbon atoms denoted as $\alpha$ and $\beta$ is selected from the group consisting of (a)   (b)   (c)

the dotted line represents the double bond present in groups (a) and (b), D is $>C=O$ or $>C=S$, $R^1$ is selected from the group consisting of cyano, lower alkanoyl and a group of the formula $-COOR^4$, $R^4$ is selected from the group consisting of methyl, ethyl, isopropyl and 2-hydroxyethyl, $R^5$ is selected from the group consisting of hydrogen, trifluoromethyl and halogen and $R^6$ is selected from the group consisting of hydrogen, trifluoromethyl, halogen and lower alkyl and either $R^2$ is hydrogen and $R^3$ is hydrogen or lower alkyl or $R^2$ and $R^3$ together are trimethylene or propenylene and the carbon atom denoted as $\gamma$ has the S- or R,S-configuration, and pharmaceutically acceptable salts thereof are presented and have utility for antagonizing the central-depressant, muscle relaxant, ataxic, blood pressure-lowering and respiratory-depressant properties of 1,4-benzodiazepines which have tranquillizing activity. They can be used, for example, as antidotes in the case of intoxications in which excessive intake of 1,4-benzodiazepines which have tranquillizing participates, or for shortening an anaesthesia induced by such 1,4-benzodiazepines. They can also be used for suppressing the activities on the central nervous system of 1,4-benzodiazepines used in other fields of indication, for example of schistosomicidally-active 1,4-benzodiazepines such as (+)-5-(o-chlorophenyl)-1,3-dihydro-3-methyl-7-nitro-2H-1,4-benzodiazepin-2-one.

Also presented are processes to produce the imidazodiazepine derivatives and intermediates therefor.

1 Claim, No Drawings

PROCESS FOR PREPARING IMIDAZODIAZEPINES

This is a division of application Ser. No. 193,775 filed Oct. 3, 1980, now U.S. Pat. No. 4,316,839.

DESCRIPTION OF THE INVENTION

The present invention relates to imidazodiazepine derivatives. More particularly, the invention is concerned with imidazo [1,5-a][1,4]diazepine derivatives of the formula

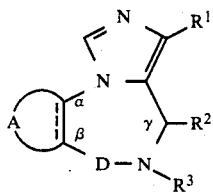

I wherein A together with the two carbon atoms denoted as α and β is selected from the group consisting of

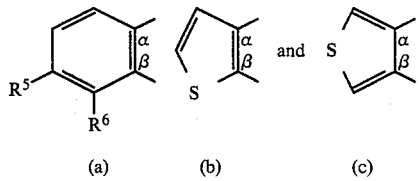

the dotted line represents the double bond present in groups (a) and (b), D is >C=O or >C=S, $R^1$ is selected from the group consisting of cyano, lower alkanoyl and a group of the formula —$COOR^4$, $R^4$ is selected from the group consisting of methyl, ethyl, isopropyl and 2-hydroxyethyl, $R^5$ is selected from the group consisting of hydrogen, trifluoromethyl and halogen and $R^6$ is selected from the group consisting of hydrogen, trifluoromethyl, halogen and lower alkyl and either $R^2$ is hydrogen and $R^3$ is hydrogen or lower alkyl or $R^2$ and $R^3$ together are trimethylene or propenylene and the carbon atom denoted as γ has the S- or R,S-configuration, and pharmaceutically acceptable acid addition salts thereof.

The aforementioned compounds are novel and possess valuable pharmacodynamic properties.

Objects of the present invention are compounds of formula I and pharmaceutically acceptable acid addition salts thereof per se and as pharmaceutically active substances, the manufacture of these compounds and intermediates in the manufacture of these compounds, medicaments containing a compound of formula I or a pharmaceutically acceptable acid addition salt thereof and the manufacture of such medicaments, as well as the use of compounds of formula I or of pharmaceutically acceptable acid addition salts thereof in the control or prevention of illnesses.

As used herein, the term "lower alkyl" denotes a straight-chain or branched-chain saturated hydrocarbon group containing at most 7, preferably at most 4, carbon atoms such as methyl, ethyl, n-propyl, isopropyl, n-butyl, sec. butyl, tert.butyl and the like. The term "lower alkanoyl" embraces groups such as acetyl, propionyl, butanoyl, sec. butanoyl and the like. The term "halogen" means fluorine, chlorine, bromine and iodine.

$R^1$ preferably represents cyano or a group of the formula —$COOR^4$ in which $R^4$ preferably represents methyl, ethyl or isopropyl.

When $R^2$ represents hydrogen, then $R^3$ preferably represents methyl. When $R^2$ and $R^3$ together represent trimethylene, then the carbon atom denoted by γ in formula I preferably has the S-configuration.

The symbol A preferably represents the group (a) hereinbefore with the dotted line signifying the double bond present in this group. In group (a), $R^5$ preferably represents hydrogen or fluorine and $R^6$ preferably represents hydrogen, fluorine, chlorine or methyl with at least one of $R^5$ and $R^6$ preferably representing hydrogen.

A particularly preferred compound of formula I is ethyl 8-fluoro-5,6-dihydro-5-methyl-6-oxo-4H-imidazo[1,5-a][1,4]benzodiazepine-3-carboxylate.

Compounds of formula I which are especially preferred are:

Ethyl 7-fluoro-5,6-dihydro-5-methyl-6-oxo-4H-imidazo[1,5-a][1,4]benzodiazepine-3-carboxylate,
ethyl 7-chloro-5,6-dihydro-5-methyl-6-oxo-4H-imidazo[1,5-a][1,4]benzodiazepine-3-carboxylate,
ethyl (S)-8-chloro-11,12,13,13a-tetrahydro-9-oxo-9H-imdiazo[1,5-a]pyrrolo[2,1-c][1,4]benzodiazepine-1-carboxylate,
ethyl (R,S)-11,13a-dihydro-9-oxo-9H-imidazo[1,5-a]pyrrolo[2,1-c][1,4]benzodiazepine-1-carboxylate and
ethyl (R,S)-8-fluoro-11,13a-dihydro-9-oxo-9H-imidazo[1,5-a]pyrrolo[2,1-c][1,4]benzodiazepine-1-carboxylate.

Other preferred compounds of formula I are:

Ethyl 5,6-dihydro-5-methyl-6-oxo-4H-imidazo[1,5-a][1,4]benzodiazepine-3-carboxylate,
methyl 5,6-dihydro-5-methyl-6-oxo-4H-imidazo[1,5-a][1,4]benzodiazepine-3-carboxylate,
isopropyl 5,6-dihydro-5-methyl-6-oxo-4H-imidazo[1,5-a][1,4]benzodiazepine-3-carboxylate,
methyl 8-fluoro-5,6-dihydro-5-methyl-6-oxo-4H-imidazo[1,5-a][1,4]benzodiazepine-3-carboxylate,
isopropyl 8-fluoro-5,6-dihydro-5-methyl-6-oxo-4H-imidazo[1,5-a][1,4]benzodiazepine-3-carboxylate,
ethyl 5,6-dihydro-5,7-dimethyl-6-oxo-4H-imidazo-[1,5-a][1,4]benzodiazepine-3-carboxylate,
ethyl (S)-11,12,13,13a-tetrahydro-9-oxo-9H-imidazo[1,5-a]pyrrolo[2,1-c][1,4]benzodiazepine-1-carboxylate,
methyl (S)-11,12,13,13a-tetrahydro-9-oxo-9H-imidazo[1,5-a]pyrrolo[2,1-c][1,4]benzodiazepine-1-carboxylate,
isopropyl (S)-11,12,13,13a-tetrahydro-9-oxo-9H-imidazo[1,5-a]pyrrolo[2,1-c][1,4]benzodiazepine-1-carboxylate,
ethyl (S)-7-fluoro-11,12,13,13a-tetrahydro-9-oxo-9H-imidazo[1,5-a]pyrrolo[2,1-c][1,4]benzodiazepine-1-carboxylate,
ethyl (S)-11,12,13,13a-tetrahydro-8-methyl-9-oxo-9H-imidazo[1,5-a]pyrrolo[2,1-c][1,4]benzodiazepine-1-carboxylate, ethyl 5,6-dihydro-5-methyl-6-thioxo-4H-imidazo[1,5-a][1,4]benzodiazepine-3-carboxylate,
ethyl 8-fluoro-5,6-dihydro-5-methyl-6-thioxo-4H-imidazo[1,5-a][1,4]benzodiazepine-3-carboxylate,
8-fluoro-5,6-dihydro-5-methyl-6-oxo-4H-imidazo[1,5-a][1,4]benzodiazepine-3-carbonitrile,
(S)-11,12,13,13a-tetrahydro-9-oxo-9H-imidazo[1,5-a]pyrrolo[2,1-c][1,4]benzodiazepine-1-carbonitrile,
5,6-dihydro-5-methyl-6-oxo-4H-imidazo[1,5-a][1,4]benzodiazepine-3-carbonitrile,
methyl (S)-10,11,12,12a-tetrahydro-8-oxo-8H-imidazo[5,1-c]pyrrolo[1,2-a]thieno[3,2-e][1,4]diazepine-1-carboxylate,
ethyl (S)-10,11,12,12a-tetrahydro-8-oxo-8H-imidazo[5,1-c]pyrrolo[1,2-a]thieno[3,2-e][1,4]diazepine-1-carboxylate,
ethyl 5,6-dihydro-5-methyl-6-oxo-4H-imidazo[1,5-a]thieno[2,3-f][1,4]diazepine-3-carboxylate and
methyl 5,6-dihydro-5-methyl-6-oxo-4H-imidazo[1,5-a]thieno[2,3-f][1,4]diazepine-3-carboxylate.

The following compounds are also representative compounds of formula I:
4,5-Dihydro-5-methyl-3-propionyl-6H-imidazo[1,5-a][1,4]benzodiazepine-6-one,
ethyl 5,6-dihydro-6-oxo-4H-imidazo[1,5-a][1,4]-benzodiazepine-3-carboxylate,
ethyl 8-fluoro-5,6-dihydro-6-oxo-4H-imidazo[1,5-a][1,4]benzodiazepine-3-carboxylate,
ethyl 8-chloro-5,6-dihydro-5-methyl-6-oxo-4H-imidazo[1,5-a][1,4]benzodiazepine-3-carboxylate,
ethyl 8-bromo-5,6-dihydro-5-methyl-6-oxo-4H-imidazo[1,5-a][1,4]-benzodiazepine-3-carboxylate,
ethyl (S)-(+)-7-chloro-11,12,13,13a-tetrahydro-9-oxo-9H-imidazo[1,5-a]pyrrolo[2,1-c][1,4]benzodiazepine-1-carboxylate,
ethyl 5,6-dihydro-5-methyl-6-oxo-4H-imidazo[1,5-a]thieno[3,4-f][1,4]diazepine-3-carboxylate,
(2-hydroxyethyl) 5,6-dihydro-5-methyl-6-oxo-4H-imidazo[1,5-a][1,4]benzodiazepine-3-carboxylate,
(2-hydroxyethyl) 8-fluoro-5,6-dihydro-5-methyl-6-oxo-4H-imidazo[1,5-a][1,4]benzodiazepine-3-carboxylate,
(2-hydroxyethyl)(S)-10,11,12,12a-tetrahydro-8-oxo-8H-imidazo[5,1-c]pyrrolo[1,2-a]thieno[3,2-e][1,4]diazepine-1-carboxylate,
ethyl (R,S)-13,13a-dihydro-9-oxo-9H-imidazo[1,5-a]pyrrolo[2,1-c][1,4]benzodiazepine-1-carboxylate,
ethyl 5,6-dihydro-5-methyl-8-trifluoromethyl-6-oxo-4H-imidazo[1,5-a][1,4]benzodiazepine-3-carboxylate,
ethyl 5,6-dihydro-5-methyl-7-trifluoromethyl-6-oxo-4H-imidazo[1,5-a][1,4]benzodiazepine-3-carboxylate,
ethyl 7-chloro-5,6-dihydro-8-fluoro-5-methyl-6-oxo-4H-imidazo[1,5-a][1,4]benzodiazepine-3-carboxylate and
ethyl (S)-8-chloro-7-fluoro-9-oxo-9H-11,12,13,13a-tetrahydro-imidazo[1,5-a]pyrrolo[2,1-c][1,4]benzodiazepine-1-carboxylate.

The imidazo[1,5-a][1,4]diazepines of formula I hereinbefore and their pharmaceutically acceptable acid addition salts can be manufactured in accordance with the present invention by
(a) reacting a compound of the general formula

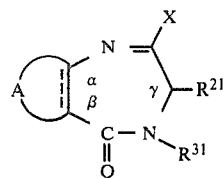

wherein A and the dotted line have the significance given earlier, X is a leaving group and either $R^{21}$ is hydrogen and $R^{31}$ is lower alkyl or $R^{21}$ and $R^{31}$ together are trimethylene or propenylene and the carbon atom denoted as $\gamma$ has the S- or R,S-configuration, in the presence of a base with an isocyanoacetic ester of the general formula

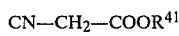

$$CN-CH_2-COOR^{41} \qquad III$$

wherein $R^{41}$ represents methyl, ethyl or isopropyl, or
(b) treating a compound of the general formula

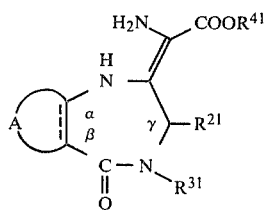

wherein A, the dotted line, $R^{21}$, $R^{31}$ and $R^{41}$ have the significance given earlier, with a formylating agent, or
(c) dehydrogenating a compound of the general formula

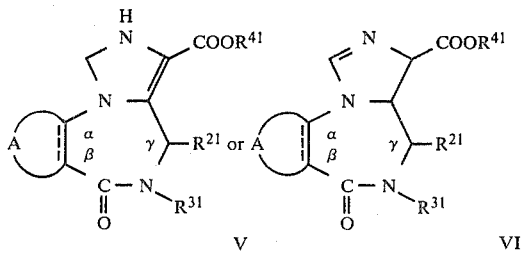

wherein A, the dotted line, $R^{21}$, $R^{31}$ and $R^{41}$ have the significance given earlier, or
(d) converting the carboxamido group in a compound of the general formula

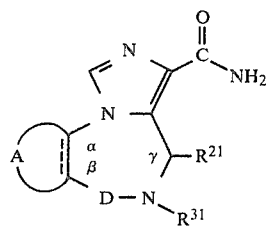

wherein A, the dotted line, D, $R^{21}$ and $R^{31}$ have the significance given earlier, into the nitrile group, or (e) appropriately substituting a compound of the general formula

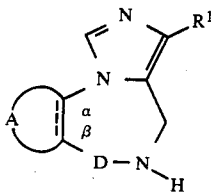

Ia wherein A, the dotted line, D and $R^1$ have the significance given earlier, at the secondary amino group, or (f) cleaving off the protecting group in a compound of the general formula

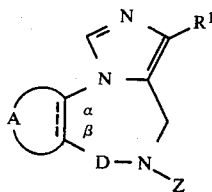

VIII wherein A, the dotted line, D and $R^1$ have the significance given earlier, and Z represents a protecting group, or (g) converting the oxime group in a compound of the general formula

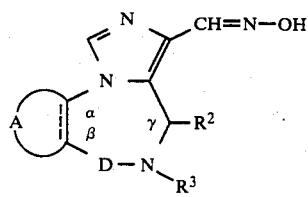

IX wherein A, the dotted line, D, $R^2$ and $R^3$ have the significance given earlier, into the nitrile group, or (h) converting the hydroxyl group in a compound of the general formula

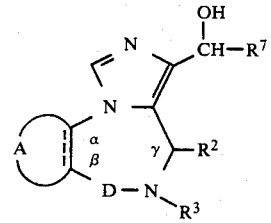

X wherein A, the dotted line, D, $R^2$ and $R^3$ have the significance given earlier and $R^7$ is lower alkyl, into the keto group, or (i) trans-esterifying a compound of the general formula

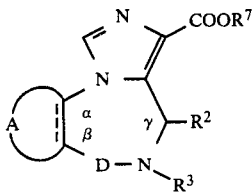

XI wherein A, the dotted line, D, $R^2$, $R^3$ and $R^7$ have the significance given earlier, or (j) converting the carbonyl group in a compound of the general formula

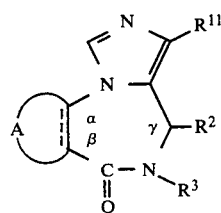

Ib wherein $R^{11}$ is cyano or a group of the formula $-COOR^4$ and A, the dotted line, $R^2$, $R^3$ and $R^4$ have the significance given earlier, into the thiocarbonyl group, and (k) if desired, converting a compound of formula I into a pharmaceutically acceptable acid addition salt.

In accordance with embodiment (a) of the process, compounds of formula I can be manufactured from compounds of formula II and isocyanoacetic esters of formula III. The leaving group denoted by the symbol X in formula II is, for example, a readily cleavable phosphinyl group, e.g. a group of the formula

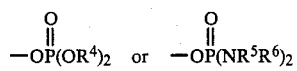

wherein $R^4$ represents lower alkyl and $R^5$ and $R^6$ each represent lower alkyl, allyl, phenyl or substituted phenyl or $R^5$ and $R^6$ together with the nitrogen atom represent an unsubstituted or substituted heterocyclic ring with 3-8 members (e.g. morpholine), a halogen atom, an alkylthio group, an aralkylthio group, an N-nitrosoalkylamino group, an alkoxy group, a mercapto group and the like (when X represents a mercapto group, then the corresponding compound of formula II is the iminothiol form of the corresponding thiolactam). The reaction of a compound of formula II with an isocyanoacetic ester of formula III is carried out in an inert solvent such as dimethylformamide, hexamethylphosphoric acid triamide, dimethyl sulphoxide, tetrahydrofuran or any other suitable inert organic solvent and in the presence of a base which is sufficiently strongly basic to form the anion of the isocyanoacetic ester of formula III. Suitable bases are alkali metal alkoxides such as sodium methoxide or potassium tert-.butoxide, alkali metal hydrides such as sodium hydride, alkali metal amides such as lithium amide or lithium diisopropylamide, tertiary amines such as triethylamine, and the like. The reaction is conveniently carried out at a temperature between about −40° C. and about room temperature.

In accordance with embodiment (b) of the process, compounds of formula I can be manufactured by treating a compound of formula IV with a formylating agent. Suitable formylating agents for this embodiment of the process are lower alkyl esters of orthoformic acid and technical equivalents thereof, for example orthoamides such as N,N-dimethylformamide dimethyl acetal, N,N,N',N',N'',N''-hexamethylmethanetriamine and the like. The reaction of a compound of formula IV with a formylating agent is conveniently carried out in the presence of an acid catalyst, for example an organic or inorganic acid such as p-toluenesulphonic acid, phosphoric acid and the like, and at room temperature or at a temperature above room temperature for example between about 25° C. and about 150° C.

In accordance with embodiment (c) of the process, compounds of formula I can be manufactured by dehydrogenating a compound of formula V or VI. Preferred reagents for this dehydrogenation include manganese dioxide, palladium-on-carbon and elemental oxygen, with atmospheric oxygen being sufficient. However, potassium permanganate, for example, can also be used. Solvents in which this dehydrogenation can be carried out include chlorinated hydrocarbons such as methylene chloride and chloroform, aromatic hydrocarbons, dimethylformamide etc. The dehydrogenation is carried out at room temperature or at a temperature above room temperature, conveniently between about 25° C. and about 200° C.

In accordance with embodiment (d) of the process, compounds of formula I can be manufactured by converting the carboxamido group in a compound of formula VII into the nitrile group. This reaction is carried out in a manner known per se using a suitable dehydrating agent such as phosphorus pentoxide or the like in an inert organic solvent such as benzene, toluene or the like at a temperature of from about 50° C. to the boiling point of the reaction mixture. Preferably, commercial phosphorus pentoxide bound to an inert carrier is used as the dehydrating agent and the reaction is carried out in boiling toluene.

In accordance with embodiment (e) of the process, compounds of formula I can be manufactured by appropriately substituting a compound of formula Ia at the secondary amino group in the 5-position. This substitution is carried out according to methods known per se using an agent yielding the desired substituent $R^{31}$; for example, a corresponding organic sulphonic acid alkyl ester (e.g. methyl p-toluenesulphonate), a corresponding dialkyl sulphate such as dimethyl sulphate or diethyl sulphate, a corresponding alkyl halide such as methyl iodide, ethyl iodide or ethyl bromide, or the like. The compound of general formula Ia is conveniently used in the form of an alkali metal salt; this is conveniently achieved by allowing the reaction to proceed in the presence of a strong base or by converting the compound of formula Ia into an alkali metal salt before the reaction with the alkylating agent. Suitable bases are alkali metal alkoxides such as sodium methoxide or potassium tert.butoxide, alkali metal hydrides such as sodium hydride, alkali metal amides such as lithium amide or lithium diisopropylamide, and the like. The reaction is conveniently carried out in the presence of an inert organic solvent. Suitable solvents for this purpose are, for example, dimethylformamide, dimethyl sulphoxide, ethyl acetate, lower alkanols and the like; many other solvents and also solvent mixtures are also suitable and their choice presents no difficulties to a person skilled in the art. The reaction temperature can be varied within fairly wide limits and generally lies between about room temperature and about the boiling point of the reaction mixture.

In accordance with embodiment (f) of the process, compounds of formula I can be manufactured by cleaving off the protecting group denoted by Z in a compound of formula VIII. In this embodiment there come into consideration only protecting groups which can be cleaved off under mild acid conditions, for example using dilute aqueous mineral acids such as dilute hydrochloric acid or dilute sulphuric acid, trifluoroacetic acid or the like, optionally with the addition of a CO-solvent such as tetrahydrofuran, dioxan, acetic acid, N,N-dimethylformamide or the like. The cleavage is conveniently carried out at a temperature between about room temperature and the boiling point of the mixture, the latter being preferred. An especially suitable protecting group is the 2,4-dimethoxybenzyl group which is conveniently cleaved off using trifluoroacetic acid, preferably at the boiling point of the mixture.

In accordance with embodiment (g) of the process, compounds of formula I can be manufactured by converting the oxime group in a compound of formula IX into the nitrile group according to methods known per se. This reaction is conveniently carried out using a suitable dehydrating agent; for example, a carboxylic acid anhydride (e.g. acetic anhydride or propionic acid anhydride), a sulphonic acid halide (e.g. p-toluenesulphonyl chloride) in the presence of a base (e.g. triethylamine or the like), and the like, the reaction temperature depending on the method used. The reaction is preferably carried out using acetic anhydride and at the boiling point of the reaction mixture.

In accordance with embodiment (h) of the process, compounds of formula I can be manufactured by oxidising the hydroxyl group in a compound of formula X according to methods known per se. Suitable oxidising agents are reagents which are generally used in such oxidations and which are known to a person skilled in the art; for example, manganese dioxide, potassium permanganate, Jones' reagents and the like. Examples of suitable solvents are, depending on the oxidising agent used, halogenated hydrocarbons such as methylene chloride, chloroform and the like, aromatic hydrocarbons such as benzene, toluene and the like, dimethylformamide, acetone, water etc. The oxidation is carried out at a temperature of from about 0° C. to the boiling point of the mixture depending on the method used. In a preferred aspect, the oxidation is carried out using manganese dioxide in a halogenated hydrocarbon such as methylene chloride, chloroform or the like, conveniently at room temperature.

In accordance with embodiment (i) of the process, compounds of formula I can be manufactured by transesterifying a compound of general formula XI, i.e. by replacing the alkyl group denoted by $R^7$ in a compound of formula XI with a group $R^4$, whereby, of course, $R^7$ and $R^4$ represent different groups. Insofar as $R^7$ in formula XI represents methyl, ethyl or isopropyl, the compounds of formula XI fall within formula I hereinbefore. $R^7$ can, of course, also represent another lower alkyl group.

This trans-esterification is carried out in a manner known per se by reacting a compound of formula XI with an alcohol corresponding to the desired group denoted by $R^4$ (i.e. methanol, ethanol, isopropanol or ethyleneglycol) at room temperature or while warming to a temperature of from about 25° C. to 150° C. Preferably, the trans-esterification is carried out in the presence of a base, with potassium cyanide or similar weak bases being especially suitable in the present case. As the solvent there is preferably used the alcohol corresponding to the group denoted by $R^4$ in the desired compound of formula I. However, the trans-esterification can also be carried out in an inert organic solvent, for example an aromatic hydrocarbon such as benzene or xylene, an ether such as dioxan, tetrahydrofuran or ethyleneglycol dimethyl ether, dimethylformamide, dimethyl sulphoxide or the like. In this trans-esterification not only a low boiling alcohol can be replaced by a high boiling alcohol, but also a high boiling alcohol can be replaced by a low boiling alcohol; it is, for example, possible to convert ethyl 5,6-dihydro-5-methyl-6-oxo-4H-imidazo[1,5-a][1,4]benzodiazepine-3-carboxylate by means of methanol into methyl 5,6-dihydro-5-methyl-6-oxo-4H-imidazo[1,5-a][1,4]benzodiazepine-3-carboxylate.

The trans-esterification can, however, also be carried out in several stages; for example, by hydrolysing a compound of formula XI to the corresponding free carboxylic acid, preparing from this a reactive functional derivative (e.g. an acid chloride or the like) and subsequently reacting this reactive carboxylic acid derivative with the alcohol corresponding to the significance of $R^4$ in the desired compound of formula I.

In accordance with embodiment (j) of the process, compounds of formula Ib can be converted into corresponding compounds of formula I in which D represents >C=S by reaction with a sulphurising agent, which can be carried out in a manner known per se. For example, the sulphurising agent can be phosphorus pentasulphide, this being preferably used in excess and the reaction being advantageously carried out in an inert organic solvent such as dioxan, methylene chloride or the like in the presence of triethylamine at a temperature of from about 50° C. to the reflux temperature of the reaction mixture. Other suitable sulphurising agents are compounds such as 2,4-bis(p-methoxyphenyl)-1,3,2,4-dithiaphosphetane-2,4-disulphide; such sulphurising agents being used in approximately the calculated amount and the reaction being carried out in the presence of an inert solvent such as toluene or xylene, conveniently at the reflux temperature of the reaction mixture or in hexamethyl-phosphoric acid triamide at a temperature between about 60° C. and 110° C.

In accordance with embodiment (k) of the process, compounds of formula I can be converted into pharmaceutically acceptable acid addition salts. The manufacture of such pharmaceutically acceptable acid addition salts is carried out according to generally usual methods. The salts provided by the present invention are salts formed with inorganic acids and with organic acids; for example, hydrochlorides, hydrobromides, sulphates, methanesulphonates, p-toluene-sulphonates, oxalates and the like.

The compounds of formula II hereinbefore used as starting materials in embodiment (a) of the process can be prepared starting from compounds of the general formula

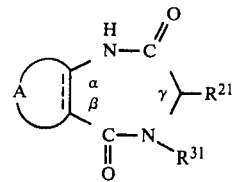   XII wherein A, the dotted line, $R^{21}$ and $R^{31}$ have the significance given earlier, according to methods known per se; see, for example, Belgian Patent Specifications Nos. 802 233, 833 249 and 865 653, U.S. Pat. No. 3,681,341 and J.Org.Chemistry 29, 231 (1964).

Various Examples hereinafter contain detailed information relating to the preparation of compounds of formula II from compounds of formula XII.

The compounds of formula XII, in turn, are known or can be readily prepared according to methods known per se; for example, by reacting a corresponding carboxylic acid anhydride of the general formula

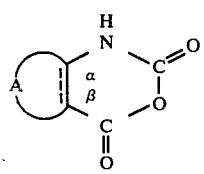   XIII wherein A and the dotted line have the significance given earlier, with an amino acid of the general formula

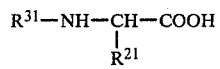   XIV wherein $R^{21}$ and $R^{31}$ have the significance given earlier.

Compounds of formula XII in which $R^{21}$ represents hydrogen and $R^{31}$ represents lower alkyl can, however, also be prepared starting from compounds of the general formula

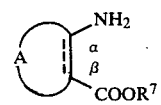   XV wherein A, the dotted line and $R^7$ have the significance given earlier, for example by treating such a compound with a reactive derivative of an α-haloacetic acid (e.g. α-chloroacetyl chloride) and reacting the intermediate obtained with a lower alkylamine (e.g. methylamine, ethylamine or the like). There are thus obtained compounds of the general formula

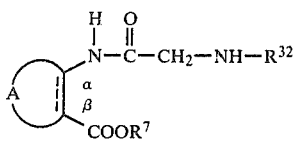  XVI wherein A, the dotted line and $R^7$ have the significance given earlier and $R^{32}$ represents lower alkyl.

By cyclising compounds of formula XVI there are obtained compounds of formula XII in which $R^{21}$ represents hydrogen and $R^{31}$ represents lower alkyl. This cyclisation is carried out, for example, by heating a corresponding compound of formula XVI for a short time at a temperature of from about 100° C. to about 300° C.

It is also possible to react a compound of formula XV with a reactive derivative of a carboxylic acid of the general formula

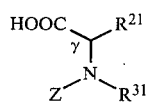  XVII wherein $R^{21}$, $R^{31}$ and Z have the significance given earlier, for example a carboxylic acid chloride or the like. After removal of the protecting group denoted by Z from a thus-obtained compound of the general formula

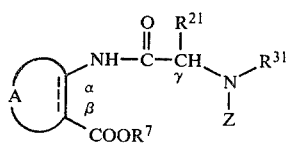  XVIII wherein A, the dotted line, $R^{21}$, $R^{31}$, $R^7$ and Z have the significance given earlier, and cyclisation in analogy to the preparation of compounds of formula XII from compounds of formula XVI, there is obtained a compound of formula XII.

In order to obtain a compound of the general formula

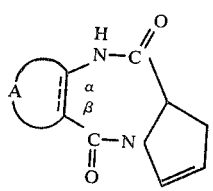  XIIa wherein A and the dotted line have the significance given earlier, the leaving group denoted by X in a compound of the general formula

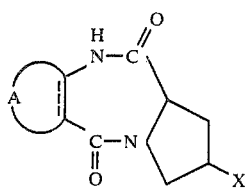  XIX wherein A and the dotted line have the significance given earlier and X represents a leaving group, can be eliminated in a manner known per se. Examples of leaving groups are sulphonic acid groups such as methane-sulphonyloxy, p-toluenesulphonyloxy and the like, halogen atoms such as chlorine, bromine and iodine, and the like. The cleavage is carried out with a base such as sodium hydride in an inert organic solvent such as dimethylformamide.

Compounds of formula XIX can be prepared in analogy to the preparation of compounds of formula XII from compounds of formulae XIII and XIV or from compounds of formula XVIII.

Compounds of formula IV used as starting materials in embodiment (b) of the process and compounds of formulae V and VI used as starting materials in embodiment (c) of the process can be prepared according to methods known per se (see Belgian Patent Specifications Nos. 833 248 and 839 364) starting from compounds of formula II in accordance with the following Reaction Scheme in which A, the dotted line, $R^{21}$, $R^{31}$, $R^{41}$ and X have the significance given earlier:

Reaction Scheme

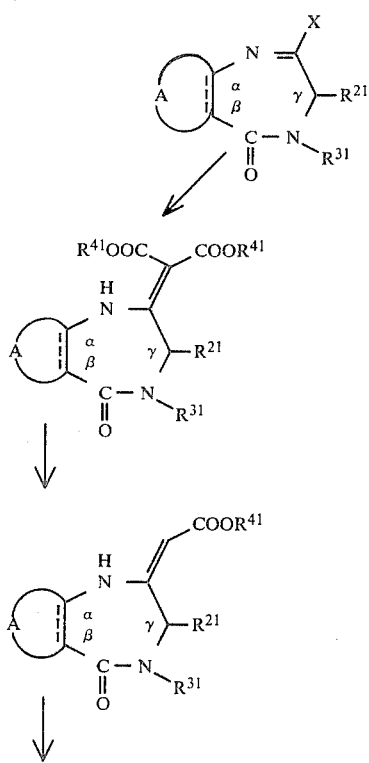

-continued
Reaction Scheme

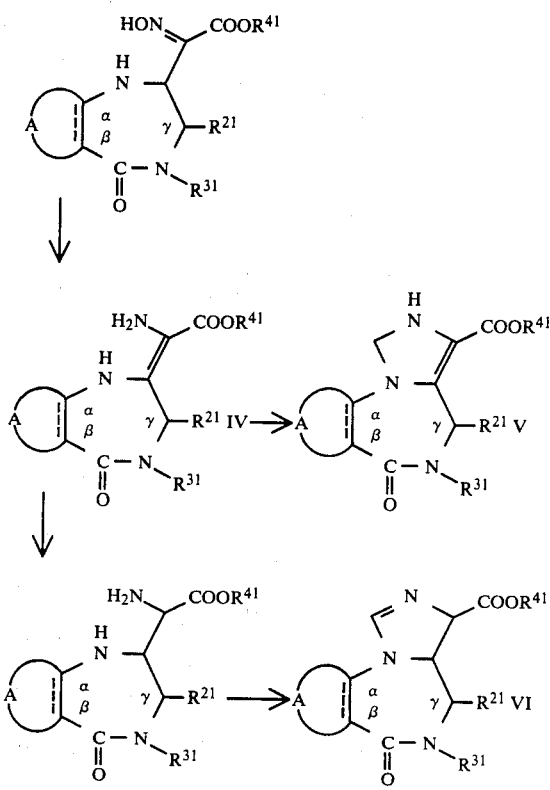

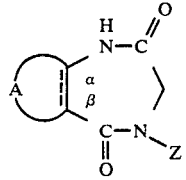 XX wherein A, the dotted line and Z have the significance given earlier, in analogy to the methods described earlier in connection with the manufacture of compounds of formula I in which $R^2$ represents hydrogen and $R^3$ represents lower alkyl, namely in analogy to embodiments (a), (b), (c), (d), (g), (h), (i) and (j) of the foregoing and to the methods described for the preparation of the corresponding starting materials.

The compounds of formula IX used as starting materials in embodiment (g) of the process are readily accessible from carboxylic acid esters of formula XI. For example, a carboxylic acid ester of formula XI can be reduced with a reduction agent such as lithium borohydride in an inert organic solvent such as diethyl ether, tetrahydrofuran, dimethoxyethane or the like to the corresponding primary alcohol which can subsequently be converted with a mild oxidising agent such as manganese dioxide or the like in an inert organic solvent such as methylene chloride, chloroform or the like into the corresponding aldehyde of the general formula

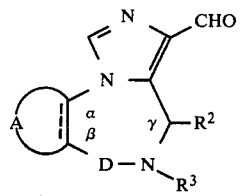 XXI

Compounds of formula VII used as starting materials in embodiment (d) of the process can be readily prepared by treating a compound of the general formula

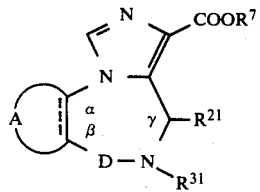 XIa wherein A, the dotted line, D, $R^{21}$, $R^{31}$ and $R^7$ have the significance given earlier, with ammonia according to methods known per se and familiar to a person skilled in the art. The amide formation can, however, also be carried out in several stages; for example, by hydrolysing the compound of formula XIa to the corresponding free carboxylic acid, preparing from this a reactive functional derivative (e.g. an acid chloride, an acid imidazolide or the like) and subsequently reacting this reactive carboxylic acid derivative with ammonia in a manner known per se.

Insofar as $R^7$ in formula XIa represents methyl, ethyl or isopropyl, the compounds of formula XIa fall within formula I hereinbefore. $R^7$ can, however, also represent another lower alkyl group.

Compounds of formula VIII used as starting materials in embodiment (f) of the process can be prepared starting from compounds of the general formula wherein A, the dotted line, D, $R^2$ and $R^3$ have the significance given earlier.

By treating an aldehyde of formula XXI with hydroxylamine there is obtained the corresponding oxime of formula IX. Conveniently, hydroxylamine hydrochloride is used as the reagent and the treatment is carried out in an inert solvent such as, for example, water, methanol or ethanol, mixtures of methanol or ethanol with water or the like, in the presence of a base such as potassium carbonate, sodium carbonate, potassium hydroxide, sodium hydroxide, triethylamine or the like, or in a basic solvent such as pyridine, triethylamine or the like at a temperature of from about room temperature to the boiling point of the mixture.

Compounds of formula X used as starting materials in embodiment (h) of the process are readily accessible from aldehydes of formula XXI. An aldehyde of formula XXI can be reacted with a metal-organic compound yielding the group $R^7$ according to methods which are generally known and familiar to a person skilled in the art. Metal-organic compounds which can be used are primarily Grignard compounds such as methyl-magnesium iodide, ethyl-magnesium iodide, isopropyl-magnesium bromide, n-propyl-magnesium bromide, n-butyl-magnesium chloride and the like and lithium alkyl compounds such as methyl lithium, ethyl lithium, isopropyl lithium, n-propyl lithium, n-butyl lithium and the like. Suitable solvents are ethers such as diethyl ether, tetrahydrofuran, tert.butyl methyl ether, mixtures thereof and the like, and, when lithium alkyl compounds are used, also hydrocarbons such as pentane, hexane, heptane, benzene, toluene and the like. Conveniently, the reaction is carried out at the boiling point of the reaction mixture, but it can also be carried out at a lower temperature (e.g. at room temperature).

Compounds of formula XI in which $R^7$ represents a group other than methyl, ethyl or isopropyl, which are used as starting materials in embodiment (i) of the process, can be prepared in analogy to the methods described earlier in connection with the preparation of compounds of formula V in which $R^1$ represents a group of the formula —$COOR^{41}$ wherein $R^{41}$ has the significance given earlier; namely in analogy to embodiments (a), (b), (c), (e), (f), and (j) of the process and to the methods described for the preparation of the corresponding starting materials. Compounds of formula XI in which $R^7$ represents other than methyl, ethyl or isopropyl are novel and also form part of the present invention.

The compounds of formulae II, IV, V, VI, VII, VIII, IX and X are novel and also form part of the present invention.

As mentioned earlier, the compounds of formula I are novel and possess extremely available pharmacodynamic properties. They have only a low toxicity, and it has been shown that they have a pronounced affinity to the central benzodiazepine receptors and are capable of antagonising the central-depressant, muscle relaxant, ataxic, blood pressure-lowering and respiratory-depressant properties of 1,4-benzodiazepines which have tranquillising activity.

The affinity of compounds of formula I to the central benzodiazepine receptors was determined according to the method described in Life Science 20, 2101–2110 (1977) and Science 198, 849–851 (1977). According to this method, the inhibition of the binding of tritiated diazepam at the specific benzodiazepine receptors in the cerebral cortex by test substances is ascertained. The $IC_{50}$ ("50% inhibiting concentration") is that concentration of the test substance which brings about a 50 percent inhibition of the specific binding of the tritiated diazepam at the specific benzodiazepine receptors in the cerebral cortex.

One of the typical properties of 1,4-benzodiazepines, which have tranquillising activity, in experimental animals is their pronounced anticonvulsive activity which can be demonstrated, for example, in the known and generally recognised pentetrazole test. This property was used as a basis for the test described hereinafter which permits the determination of compounds which are capable of antagonising the central properties of 1,4-benzodiazepines which have tranquillising activity.

In this test, 5 mg/kg (i.p.) of diazepam (a supramaximal dosage, which in the pentetrazole test on more than 900 mice protected all experimental animals from spasmodic seizures) were administered to mice 1 hour before the pentetrazole (120 mg/kg, i.p.) and the compound to be tested was administered 15 minutes before the pentetrazole. The antagonistic activity of the compounds tested, i.e. their ability to counteract the activity of diazepam in the pentetrazole test, is determined by counting the mice which suffer spasmodic seizures in this test.

In the following Table there are compiled the results which have been obtained with representative compounds of formula I. The $ED_{50}$ value is given for each compound listed in the Table. The $ED_{50}$ is the amount of the test compound in mg/kg (p.o.) which counteracts in 50% of the animals the diazepam effect in the foregoing test. Moreover, the Table contains the $IC_{50}$ value (defined hereinbefore) for all test compounds listed therein as well as details concerning the acute toxicity of certain compounds ($LD_{50}$ in mg/kg following single oral administration to mice).

TABLE

Imidazo[1,5-a][1,4]benzodiazepine derivatives, i.e. compounds of formula I in which A represents group (a)

| $R^1$ | $R^2$ | $R^3$ | Configuration | $R^5$ | $R^6$ | D | $IC_{50}$ in $\mu M/l$ | $ED_{50}$ in mg/kg p.o. | $LD_{50}$ in mg/kg p.o. |
|---|---|---|---|---|---|---|---|---|---|
| —$COOC_2H_5$ | H | —$CH_3$ | — | F | H | C=O | 2.5 | 5.8 | >5000 |
| —$COOC_2H_5$ | —$(CH_2)_3$— | | S | H | H | C=O | 6.4 | 9.3 | 1250–2500 |
| —$COOC_2H_5$ | H | —$CH_3$ | — | H | H | C=O | 3.0 | 10.9 | >5000 |
| —$COOC_2H_5$ | H | —$CH_3$ | — | H | H | C=S | 6.0 | 8.9 | |
| —$COOCH_3$ | H | —$CH_3$ | — | H | H | C=O | 9.0 | 13.5 | |
| —$COOCH(CH_3)_2$ | H | —$CH_3$ | — | H | H | C=O | 12.0 | 7.0 | |
| —$COOCH_3$ | H | —$CH_3$ | — | F | H | C=O | 6.0 | 4.9 | |
| —$COOCH(CH_3)_2$ | H | —$CH_3$ | — | F | H | C=O | 3.9 | 6.6 | >5000 |
| —$COOC_2H_5$ | H | —$CH_3$ | — | H | F | C=O | 2.0 | 2.1 | >5000 |
| —$COOC_2H_5$ | H | —$CH_3$ | — | H | Cl | C=O | 3.0 | 0.48 | |
| —$COOC_2H_5$ | H | —$CH_3$ | — | H | —$CH_3$ | C=O | 5.0 | 7.1 | |
| —$COOCH_3$ | —$(CH_2)_3$— | | S | H | H | C=O | 32.0 | 3.5 | 2000–4000 |
| —$COOCH(CH_3)_2$ | —$(CH_2)_3$— | | S | H | H | C=O | 3.0 | 18.6 | |
| —$COOC_2H_5$ | —$(CH_2)_3$— | | S | F | H | C=O | 6.0 | 8.9 | |
| —$COOC_2H_5$ | —$(CH_2)_3$— | | S | H | Cl | C=O | 1.7 | 1.0 | 750–1500 |
| —$COOC_2H_5$ | —$(CH_2)_3$— | | S | H | —$CH_3$ | C=O | 5.0 | 6.5 | |
| —$COOC_2H_5$ | H | —$CH_3$ | — | F | H | C=S | 2.5 | 6.3 | |
| —CN | H | —$CH_3$ | — | H | H | C=O | 100.0 | 2.6 | 1250 |
| —CN | H | —$CH_3$ | — | F | H | C=O | 93.0 | 4.2 | |
| —CN | —$(CH_2)_3$— | | S | H | H | C=O | 31.0 | 12.1 | |
| —$COOC_2H_5$ | —CH=CH—$CH_2$— | | R/S | H | H | C=O | 2.3 | 3.9 | |
| —$COOC_2H_5$ | —CH=CH—$CH_2$— | | R/S | H | F | C=O | 2.1 | 1.8 | 500–1000 |

Imidazo[1,4-a]thieno[2,3-f]1,4] diazepine derivatives, i.e. compounds of formula I wherein A signifies the group (b):

| $R^1$ | $R^2$ | $R^3$ | D | Configuration | $IC_{50}$ in $\mu M/l$ | $ED_{50}$ in mg/kg p.o. |
|---|---|---|---|---|---|---|
| —$COOCH_3$ | —$(CH_2)_3$— | | C=O | S | 2.1 | 0.22 |
| —$COOC_2H_5$ | —$(CH_2)_3$— | | C=O | S | 0.9 | 1.3 |

-continued

| Imidazo[1,4-a]thieno[2,3-f][1,4]diazepine derivatives, i.e. compounds of formula I wherein A signifies the group (b): | | | | | | |
|---|---|---|---|---|---|---|
| $R^1$ | $R^2$ | $R^3$ | D | Config-uration | $IC_{50}$ in $\mu M/l$ | $ED_{50}$ in mg/kg p.o. |
| $-COOC_2H_5$ | H | $-CH_3$ | C=O | — | 1.1 | 12.6 |
| $-COOCH_3$ | H | $-CH_3$ | C=O | — | 1.2 | 0.83 |

From the tests described hereinafter it is evident that one compound of formula I, ethyl 5,6-dihydro-5-methyl-6-oxo-4H-imidazo[1,5-a][1,4]benzodiazepine-3-carboxylate referred to as "test substance" hereinafter), antagonises the central activities of the known 1,4-benzodiazepine derivative diazepam:

Male albino rats (body weight about 165 g) are used for this test. Diazepam is administered to these animals in a dosage of 5 mg/kg i.v., so that they fall asleep immediately, no longer show rousing reflex, sleep for at least 60 minutes in the lateral position and slowly wake up after about 1.5 hours; if diazepam is administered to the animals in a dosage of 10 mg/kg i.p., they fall asleep within a few minutes, sleep for ca 2-3 hours and then slowly wake up. If the test substance in a dosage of 5 mg/kg i.v. is given to the animals 5 or 15 minutes after the administration of 5 mg/kg i.v. of diazepam or 30 minutes after the administration of 10 mg/kg i.p. of diazepam, then the animals stand up immediately and move around, this waking phase lasting for 30 minutes to 1 hour.

If the test substance is given to the animals in a dosage of b 20 mg/kg i.p., then the animals remain awake and show a normal behaviour; if diazepam is then administered to them after 30 minutes in a dosage of 5 mg/kg i.v., then they show in the first 2 minutes after the injection slight sedation and ataxia, but these symptoms rapidly disappear and the waking phase lasts for at least 30 minutes.

From the tests described hereinafter it is evident that one compound of formula I, ethyl (S)-11,12,13,13a-tetrahydro-9-oxo-9H-imidazo[1,5-a]-pyrrolo[2,1-c][1,4]benzodiazepine-1-carboxylate (referred to as "test substance" hereinafter), antagonises the central activities of the known 1,4-benzodiazepine derivative flunitrazepam:

Four tests were carried out on conscious, curarised, artificially respirated rats. The bipolar-derived EEG of the dorsal hippocampus served as the measured variable. 10 minutes after the beginning of the derivation flunitrazepam was administered intravenously in a dosage of 0.1 mg/kg. The test substance was likewise administered intravenously in a dosage of 1 mg/kg to one animal 10 minutes and to three animals 30 minutes after the administration of flunitrazepam. The EEGs obtained were analysed continuously in the frequency range according to the rules of the Fourier transformation, whereby each of the computed spectra related to 1 minute.

The normal EEG from the hippocampus of conscious, curarised rats is characterised by a stable theta rhythm of 3.75-4.25 Hertz which remains unchanged at least 3 hours after the beginning of the artificial respiration. Flunitrazepam, in the given dosage, completely suppresses this theta rhythm for about 15 minutes. Thereafter, there appears a rhythm which is slowed down to 2.75-3.25 Hertz, which increases continuously and again attains the normal frequency of 4 Hertz 1 to 1.5 hours after the injection.

The test substance leads, in the specified dosage and at the specified times after flunitrazepam, to an immediate, long-lasting normalisation of the described theta rhythm at 4 Hertz. When the test substance was administered 10 minutes after flunitrazepam, then it immediately brought about the rhythm suppressed by flunitrazepam, whereby this showed the normal frequency from the outset. When the test substance was administered 30 minutes after flunitrazepam, then it accelerated the already, but slowly, re-appearing rhythm immediately to its normal frequency of 4 Hertz.

As mentioned earlier, compounds of formula I antagonise the central-depressant, muscle relaxant, ataxic, blood pressure-lowering and respiratory-depressant properties of 1,4-benzodiazepines which have tranquillising activity. The latter are in widespread use in therapy and are often administered in high dosages, so that the above-mentioned activities can also appear strongly as side-effects. The compounds of formula I can be used as antidotes in the case of intoxications in which excessive intake of 1,4-benzodiazepines which have tranquillising activity participates. They are also suitable for shortening anaesthesia in surgery and in obstetrics induced by 1,4-benzodiazepines which have tranquillising activity. In the case of neonatals, a possible respiratory depression, which is caused by the administration of 1,4-benzodiazepines which have tranquillising activity to the mother, can be counteracted. The compounds of formula I can also be used to suppress, in the case of 1,4-benzodiazepines which are used in other fields of indication, the activities on the central nervous system which are undesirable in such fields. Examples of such 1,4-benzodiazepines which can be used in other fields of indication are schistosomicidally-active 1,4-benzodiazepine derivatives of the general formulae

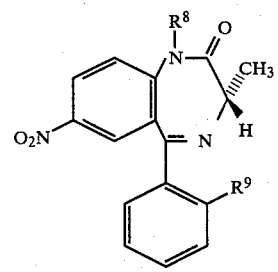

XXII wherein $R^8$ is hydrogen or lower alkyl and $R^9$ is halogen, and

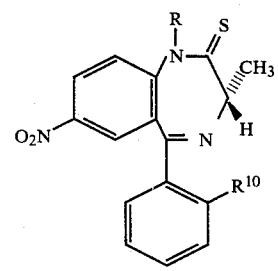

XXIII wherein R is hydrogen or lower alkyl and $R^{10}$ is selected from the group consisting of hydrogen, halogen or trifluoromethyl, which are described in British Patent Nos. 1,444,529 and 1,474,305. An example of such a schistosomicidally-active 1,4-benzodiazepine derivative is (+)-5-(o-chlorophenyl)-1,3-dihydro-3-methyl-7-nitro-2H-1,4-benzodiazepin-2-one.

The following tests show that representative compounds of formula I, which suppress the strong, but undesirable, central activities of the highly active schistosomicide (+)-5-(o-chlorophenyl)-1,3-dihydro-3-methyl-7-nitro-2H-1,4-benzodiazepin-2-one on the central nervous system, are in no way detrimental to its schistosomicidal activity.

Mice and golden hamsters are infected subcutaneously with 60 cercaria of Schistosoma mansoni. Ca 42 days after the infection, they are treated orally with a single dosage of the compound to be tested. 5 animals are used per test preparation and dosage. 10 untreated animals are used as controls. The animals are killed and dissected 2 weeks (hamster) or 3 weeks (mice) after the treatment. Worm pairs in mesenteric veins, portal vein and liver are dissected-out, counted and the condition of the worms (living or dead) is registered. A schistosomicidal activity of a test preparation manifests itself in the appearance of dead worms in the vessels of the liver. Dead worms are never found in untreated control animals. The test is evaluated by calculating the percentage of dead worm pairs in the vessels of the liver in infected, treated animals.

In order to test the in vitro activity of preparations, worm pairs of Schistosoma mansoni are isolated from mice and incubated at 37° C. in a nutrient medium. Test preparations are added in the form of a solution or as a suspension. The motility of the worms is observed under the microscope and registered during the test duration of 120 hours. A schistosomicidal activity of a test preparation manifests itself in the more or less rapid loss of motility of the worms. Control worms in the nutrient medium without the addition of test preparation maintain their normal motility during the entire test duration of 120 hours.

The following representative compounds of formula I were tested in tests described earlier for possible detrimental effects on the schistosomicidal activity of (+)-5-(o-chlorophenyl)-1,3-dihydro-3-methyl-7-nitro-2H-1,4-benzodiazepin-2-one (compound S).

| | |
|---|---|
| Ethyl 8-fluoro-5,6-dihydro-5-methyl-6-oxo-4H-imidazo[1,5-a][1,4]benzodiazepine-3-carboxylate | (compound A); |
| ethyl (S)-11,12,13,13a-tetrahydro-3-oxo-9H-imidazo[1,5-a]pyrrolo[2,1-c][1,4]-benzodiazepine-1-carboxylate | (compound B); |
| ethyl 5,6-dihydro-5-methyl-6-oxo-4H-imidazo[1,5-a][1,4]benzodiazepine-3-carboxylate | (compound C); |
| and | |
| ethyl 5,6-dihydro-5-methyl-6-thioxo-4H-imidazo[1,5-a][1,4]benzodiazepine-3-carboxylate | (compound D). |

As is evident from the following compilations relating to the results on test animals and in the in vitro test, the schistosomicidal activity of (+)-5-(o-chlorophenyl)-1,3-dihydro-3-methyl-7-nitro-2H-1,4-benzodiazepin-2-one (compound S) was not influenced detrimentally by any of the compounds of general formula I which were tested.

Test results in mice and hamsters

| Host | Dosage in mg/kg p.o. | | Dosage ratio | Schistoso-micidal activity in % |
|---|---|---|---|---|
| | Compound S | Compound A | | |
| Mouse | 75 | — | — | 99 |
| | — | 750 | — | 0 |
| | 75 | 225 | 1:3 | 98 |
| | 75 | 750 | 1:10 | 93 |
| | — | — | — | 0 |
| Hamster | 75 | — | — | 100 |
| | 75 | 225 | 1:3 | 100 |
| | — | — | — | 0 |
| | Compound S | Compound B | | |
| Mouse | 75 | 300 | 1:4 | 91 |
| Hamster | 75 | 300 | 1:4 | 91 |
| | Compound S | Compound C | | |
| Mouse | 75 | 150 | 1:2 | 99 |
| Hamster | 75 | 150 | 1:2 | 100 |
| | Compound S | Compound D | | |
| Mouse | 75 | 150 | 1:2 | 93 |
| | 75 | 750 | 1:10 | 98 |
| Hamster | 75 | 150 | 1:2 | 100 |

Results of in vitro experiments

| Preparation concentration in μg/ml | | Concentration ratio | Activity* |
|---|---|---|---|
| Compound S | Compound A | | |
| 25 | — | — | a |
| — | 75 | — | b |
| — | 750 | — | b |
| 25 | 75 | 1:3 | a |
| 25 | 750 | 1:10 | a |
| — | — | — | b |
| Compound S | Compound B | | |
| — | 100 | — | b |
| 25 | 100 | 1:4 | a |
| Compound S | Compound C | | |
| — | 100 | — | b |
| 25 | 50 | 1:2 | a |
| Compound S | Compound D | | |
| — | 50 | — | b |
| — | 250 | — | b |
| 25 | 50 | 1:2 | a |
| 25 | 250 | 1:10 | a |

Activity:
a = worm pairs motionless within 15 minutes;
b = worm pairs show normal motility during the test duration of 120 hours.

The compounds of formula I and their pharmaceutically acceptable acid addition salts can be used as medicaments, for example in the form of pharmaceutical preparations. The pharmaceutical preparations can be administered orally, for example in the form of tablets, coated tablets, dragees, hard and soft gelatin capsules, solutions, emulsions or suspensions. The administration can, however, also be carried out rectally (e.g. in the form of suppositories) or parenterally (e.g. in the form of injection solutions).

For the manufacture of tablets, coated tablets, dragees and hard gelatin capsules, the compounds of formula I and their pharmaceutically acceptable acid addition salts can be processed with pharmaceutically inert, inorganic or organic carriers. Examples of such carriers which can be used for tablets, dragees and hard gelatin capsules are lactose, maize starch or derivatives thereof, talc, stearic acid or its salts etc.

Suitable carriers for soft gelatin capsules are, for example, vegetable oils, waxes, fats, semi-solid and liquid polyols etc.

Suitable carriers for the manufacture of solutions and syrups are, for example, water, polyols, saccharose, invert sugar, glucose and the like.

Suitable carriers for injection solutions are, for example, water, alcohols, polyols, glycerine, vegetable oils etc.

Suitable carriers for suppositories are, for example, natural or hardened oils, waxes, fats, semi-liquid or liquid polyols and the like.

The pharmaceutical preparations can also contain preserving agents, solubilising agents, stabilising agents, wetting agents, emulsifiers, sweetening agents, colouring agents, flavouring agents, salts for varying the osmotic pressure, buffers, coating agents or antioxidants. They can also contain still other therapeutically valuable substances.

As mentioned earlier, compounds of formula I and pharmaceutically acceptable acid addition salts thereof can be used in accordance with the invention in the control or prevention of illnesses, especially in the antagonisation of the central-depressant muscle relaxant, ataxic, blood pressure-lowering and respiratory-depressant properties of 1,4-benzodiazepines which have tranquillising activity. In particular, compounds of formula I can be used in the control of schistosomiasis in combination with the schistosomicidally-active 1,4-benzodiazepine derivatives of formula XXII and/or XXIII mentioned earlier. In this case, ethyl 8-fluoro-5,6-dihydro-5-methyl-6-oxo-4H-imidazo[1,5-a][1,4]benzodiazepine-3-carboxylate is preferably used as the compound of formula I and (±)-5-(o-chlorophenyl)-1,3-dihydro-3-methyl-7-nitro-2H-1,4-benzodiazepin-2-one is preferably used as the schistosomicidally-active 1,4-benzodiazepine derivative. The compounds of formula I or their pharmaceutically acceptable acid addition salts can be administered before, simultaneously with or after the administration or intake of 1,4-benzodiazepines which have tranquillising activity. If the compound of formula I or a pharmaceutically acceptable acid addition salt thereof is administered simultaneously with the 1,4-benzodiazepine which has tranquillising activity, then this administration can be as an ad-hoc combination or in the form of a pharmaceutical combination which contains a compound of formula I or a pharmaceutically acceptable acid addition salt thereof and a 1,4-benzodiazepine derivative which has tranquillising activity; said pharmaceutical combinations also form part of the present invention. The dosage of compounds of formula I and their pharmaceutically acceptable acid addition salts can vary within wide limits and is, of course, fitted to the individual requirements in each particular case. In general, a daily dosage of about 2 mg to about 500 mg should be appropriate.

As mentioned earlier, medicaments containing a compound of formula I or a pharmaceutically acceptable acid addition salt thereof also form part of the present invention, as does a process for the manufacture of such medicaments which comprises bringing one or more compounds of formula I or pharmaceutically acceptable acid addition salts thereof and, if desired, one or more other therapeutically valuable substances into a galenical administration form; in this connection reference is again made to the pharmaceutical combinations mentioned earlier which also form part of the present invention. In particular, pharmaceutical combinations containing a compound of formula I and a benzodiazepine derivative of formula XXII and/or XXIII, preferably combinations containing ethyl 8-fluoro-5,6-dihydro-5-methyl-6-oxo-4H-imidazo[1,5-a][1,4]benzodiazepine-3-carboxylate and (±)-5-(o-chlorophenyl)-1,3-dihydro-3-methyl-7-nitro-2H-1,4-benzodiazepin-2-one, form part of the present invention. Such combinations are suitable for the control of schistosomiasis.

The following Examples illustrate the present invention:

EXAMPLE 1

(a) 24 g (132.5 mmol) of 5-fluoroisatoic acid anhydride are dissolved in 140 ml of dimethyl sulphoxide and treated with 11.8 g (132.5 mmol) of sarcosine. The solution is stirred at 100° C. until the gas evolution ceases (duration: ca 1.5 hours) and subsequently poured into ca 1.2 liters of water. After stirring for 10 minutes, a solid crystallises out. The crystals are filtered off under suction, washed with 1 liter of water and dried. There is obtained 7-fluoro-3,4-dihydro-4-methyl-2H-1,4-benzodiazepine-2,5(1H)-dione of melting point 262°–263° C.

(b) A solution of 6.5 g (32 mmol) of 7-fluoro-3,4-dihydro-4-methyl-2H-1,4-benzodiazepine-2,5(1H)-dione in 30 ml of dry dimethylformamide is treated with 4,3 g (38 mmol) of potassium tert.butylate under an argon atmosphere. The temperature thereby rises to 35° C. After 10 minutes, the mixture is cooled to −30° C. and 5.8 g (34 mmol) of diethylchlorophosphate are added dropwise thereto at −30° C. to −20° C. The solution is subsequently stirred at −20° C. for 10 minutes.

Separately, 4 g (35 mmol) of potassium tert.butylate are dissolved in 10 ml of dimethylformamide and treated at ca −40° C. with 4 g (35 mmol) of ethyl isocyanoacetate. This solution is added dropwise at −10° C. to −20° C. to the mixture obtained according to the preceding paragraph. The resulting mixture is then stirred without cooling for 1 hour, 3.2 ml of glacial acetic acid are added thereto, the mixture is poured into ca 400 ml of water and extracted three times with 150 ml of ethyl acetate each time. The combined organic extracts are washed five times with 200 ml of water each time, dried over magnesium sulphate and evaporated. From the oily residue there is obtained, by column chromatography on silica gel and subsequent recrystallisation from ethyl acetate and ether, ethyl 8-fluoro-5,6-dihydro-5-methyl-6-oxo-4H-imidazo[1,5-a][1,4]benzodiazepine-3-carboxylate of melting point 199°–200° C.

EXAMPLE 2

(a) A mixture of 20.82 g (100 mmol) of 7-fluoro-3,4-dihydro-4-methyl-2H-1,4-benzodiazepine-2,5(1H)-dione and 200 ml of chloroform is heated to boiling under reflux for 2.5 hours with 121.18 g (1 mol) of dimethylaniline and 23 g (150 mmol) of phosphorus oxychloride. The solution is poured into a mixture of 71 g of sodium bicarbonate and 500 ml of water and stirred for 0.5 hour. The mixture is extracted twice with chloroform, the chloroform phases are washed with water and dried over magnesium sulphate. After removal of the solvent, there are obtained 162.2 g of a yellow solution of the corresponding iminochloride in dimethylaniline.

Separately, 8.41 g (75 mmol) of potassium tert.butylate are dissolved in 30 ml of dimethylformamide and treated at ca 40° C. with 8.48 g (75 mmol) of ethyl isocyanoacetate. To this solution are added dropwise at −5° C. to 0° C. 81.1 g of the foregoing iminochloride solution in dimethylaniline and the mixture obtained is stirred without cooling for 10 minutes before it is neutralised with 7.5 ml of acetic acid. The mixture is poured into water and extracted three times with chloroform. The chloroform extracts are washed five times with water, dried over magnesium sulphate and evaporated. By recrystallisation of the crude product from alcohol there is obtained ethyl 8-fluoro-5,6-dihydro-5-methyl-6-oxo-4H-imidazo[1,5-a][1,4]benzodiazepine-3-carboxylate of melting point 200°–203° C.

(b) The remaining 81.1 g of the iminochloride solution in dimethylaniline, obtained according to paragraph (a), are added dropwise at 0° C. to a pre-cooled solution of 7.59 g (75 mmol) of triethylamine and 8.48 g (75 mmol) of ethyl isocyanoacetate in 30 ml of dimethylformamide. After stirring at room temperature overnight, the light brown solution is diluted with water and extracted three times with chloroform. The combined chloroform extracts are washed five times with water, dried over magnesium sulphate and evaporated. The residue is recrystallised from alcohol and gives ethyl 8-fluoro-5,6-dihydro-5-methyl-6-oxo-4H-imidazo[1,5-a][1,4]benzodiazepine-3-carboxylate of melting point 201°–203° C.

EXAMPLE 3

A mixture of 3.5 g (11.5 mmol) of ethyl 8-fluoro-5,6-dihydro-5-methyl-6-oxo-4H-imidazo[1,5-a][1,4]benzodiazepine-3-carboxylate, 0.15 g of potassium cyanide and 40 ml of methanol is stirred at the boiling point for 2.5 hours. The solvent is distilled off on a rotary evaporator and the residue is taken up in chloroform. After filtration from insoluble material, the filtrate is concentrated. After recrystallisation of the residue from ethyl acetate, there is obtained methyl 8-fluoro-5,6-dihydro-5-methyl-6-oxo-4H-imidazo[1,5-a][1,4]benzodiazepine-3-carboxylate of melting point 195°–196.5° C.

EXAMPLE 4

100 ml of 2-propanol are treated with 100 mg of sodium hydride. 5 g of ethyl 8-fluoro-5,6-dihydro-5-methyl-6-oxo-4H-imidazo[1,5-a][1,4]benzodiazepine-3-carboxylate are added thereto and the mixture is heated to boiling under reflux for 1 hour. Subsequently, the mixture is left to cool to room temperature, the separated crystals are filtered off and washed with 2-propanol and water, there being obtained isopropyl 8-fluoro-5,6-dihydro-5-methyl-6-oxo-4H-imidazo[1,5-a][1,4]benzodiazepine-3-carboxylate of melting point 243°–244° C.

EXAMPLE 5

A mixture of 6.08 g (20 mmol) of ethyl 8-fluoro-5,6-dihydro-5-methyl-6-oxo-4H-imidazo[1,5-a][1,4]benzodiazepine-3-carboxylate, 100 mg of potassium cyanide and 60 ml of ethyleneglycol is stirred at 130° C. for 6 hours and subsequently evaporated. After taking up the residue in chloroform, the solution is washed with water, dried over magnesium sulphate and evaporated. After recrystallisation of the crude product from ethyl acetate, there is obtained 2-hydroxyethyl 8-fluoro-5,6-dihydro-5-methyl-6-oxo-4H-imidazo[1,5-a][1,4]benzodiazepine-3-carboxylate of melting point 202°–204° C.

EXAMPLE 6

10.7 g (35.3 mmol) of ethyl 8-fluoro-5,6-dihydro-5-methyl-6-oxo-4H-imidazo[1,5-a][1,4]benzodiazepine-3-carboxylate and 7.13 g (17.6 mmol) of 2,4-bis(p-methoxyphenyl)-1,3,2,4-dithiadiphosphetane-2,4-disulphide in 100 ml of toluene are heated to boiling under reflux for 22 hours. The mixture is subsequently concentrated in vacuo until crystallisation begins and is then left to stand in an ice-bath for 1 hour. The crystallised-out material is filtered off under suction and washed with a small amount of toluene. The mixture is separated on silica gel with ethyl acetate/chloroform (1:9). After recrystallisation from ethyl acetate, there is obtained pure ethyl 8-fluoro-5,6-dihydro-5-methyl-6-thioxo-4H-imidazo[1,5-a][1,4]benzodiazepine-3-carboxylate of melting point 157°–159° C.

EXAMPLE 7

(a) 15.0 g (49.5 mmol) of ethyl 8-fluoro-5,6-dihydro-5-methyl-6-oxo-4H-imidazo[1,5-a][1,4]benzodiazepine-3-carboxylate are dissolved under argon in 450 ml of boiling absolute tetrahydrofuran (filtered over Alox) and added dropwise at 50° C. to a solution of 1.1 g (49.5 mmol) of lithium borohydride in 50 ml of absolute tetrahydrofuran. The mixture is stirred at 40° C. for 4 hours and at the boiling point for 2.5 hours. Subsequently, the mixture is decomposed at 40° C. with 20 ml of water and 20 ml of concentrated hydrochloric acid/water (1:1) and stirred at room temperature overnight. After removal of the tetrahydrofuran in vacuo, the residue is treated with 14 ml of concentrated ammonia. The mixture is left to crystallise in the cold and separated material is filtered off under suction and washed with water. After recrystallisation from ethanol, there is obtained 8-fluoro-4,5-dihydro-3-(hydroxymethyl)-5-methyl-6H-imidazo[1,5-a][1,4]benzodiazepin-6-one of melting point 221°–223° C.

(b) A suspension of 4.93 g (18.9 mmol) of 8-fluoro-4,5-dihydro-3-(hydroxymethyl)-5-methyl-6H-imidazo[1,5-a][1,4]-benzodiazepin-6-one in 220 ml of methylene chloride is treated with 30 g of manganese dioxide and the mixture is stirred at room temperature of 1.5 hours. After filtration over Dicalit, the filtrate is evaporated in vacuo and the residue is recrystallised from ethanol. There is thus obtained 8-fluoro-5,6-dihydro-5-methyl-6-oxo-4H-imidazo[1,5-a][1,4]benzodiazepine-3-carboxaldehyde of melting point 224°–226° C.

(c) A solution of 4.14 g (14.5 mmol) of sodium carbonate decahydrate in 20 ml of water is added dropwise to a mixture of 3.0 g (11.6 mmol) of 8-fluoro-5,6-dihydro-5-methyl-6-oxo-4H-imidazo[1,5-a][1,4]benzodiazepine-3-carboxaldehyde, 0.99 g (14.5 mmol) of hydroxylamine hydrochloride and 60 ml of water, the mixture is stirred at 70° C. for 1 hour, cooled in an ice-bath and the separated material is filtered off under suction and washed with water. The still moist substance is recrystallised from ethanol and yields 8-fluoro-5,6-dihydro-5-methyl-6-oxo-4H-imidazo[1,5-a][1,4]benzodiazepine-3-carboxaldehyde-3-oxime of melting point 247°–250° C.

(d) 1.65 g (6 mmol) of 8-fluoro-5,6-dihydro-5-methyl-6-oxo-4H-imidazo[1,5-a][1,4]benzodiazepine-3-carboxaldehyde-3-oxime are heated to boiling under reflux for 4.5 hours in 15 ml of acetic acid anhydride and the mixture is evaporated. The residue is taken up in 100 ml of chloroform and the solution is washed once with saturated sodium hydrogen carbonate solution and once with water. The chloroform solution is dried over magnesium sulphate and concentrated. After column chromatography and recrystallisation from ethyl acetate, there is obtained 8-fluoro-5,6-dihydro-5-methyl-6-oxo-4H-imidazo[1,5-a][1,4]benzodiazepine-3-carbonitrile of melting point 236°–237° C.

EXAMPLE 8

(a) A solution of 23.7 g of 5-fluoroisatoic acid anhydride and 29.5 g of N-(2,4-dimethoxybenzyl)-glycine in 130 ml of dimethyl sulphoxide is heated at 100° C. for 1.5 hours. The mixture is cooled to room temperature and poured into 400 ml of water. The separated product is filtered off under suction and washed with water. There is thus obtained 4-(2,4-dimethoxybenzyl)-7-fluoro-3,4-dihydro-2H-1,4-benzodiazepine-2,5(1H)-dione of melting point 190°–192° C.

(b) 27 g (78 mmol) of 4-(2,4-dimethoxybenzyl)-7-fluoro-3,4-dihydro-2H-1,4-benzodiazepine-2,5(1H)-dione are placed in 75 ml of dry dimethylformamide and treated with 9.6 g (86 mmol) of potassium tert.butylate. The temperature rises to 40° C. and the solution is stirred at room temperature for 10 minutes before it is cooled to −30° C. At this temperature there are added dropwise 14.2 g (82 mmol) of diethylchlorophosphate and the mixture is stirred at −20° C. for 10 minutes.

Separately, 9.7 g (86 mmol) of potassium tert.butylate are dissolved in 20 ml of dry dimethylformamide, the solution is cooled to −50° C. and treated with 9.8 g (86 mmol) of ethyl isocyanoacetate. This solution is immediately added dropwise at −20° C. to −10° C. to the mixture obtained according to the preceding paragraph. The resulting mixture is stirred without cooling for 1 hour, 7.8 ml of glacial acetic acid are added thereto, the mixture obtained is poured into 1 liter of water and extracted three times with 200 ml of ethyl acetate each time. The combined organic extracts are washed five times with 250 ml of water each time, dried over magnesium sulphate and evaporated. After recrystallisation from 150 ml of ethyl acetate, there is obtained ethyl 5-(2,4-dimethoxybenzyl)-8-fluoro-5,6-dihydro-6-oxo-4H-imidazo[1,5-a][1,4]benzodiazepine-3-carboxylate of melting point 159°–160° C.

(c) 13.0 g (29.6 mmol) of ethyl 5-(2,4-dimethoxybenzyl)-8-fluoro-5,6-dihydro-6-oxo-4H-imidazo[1,5-a][1,4]benzodiazepine-3-carboxylate are heated to boiling under reflux for 4 hours in 45 ml of trifluoroacetic acid. After evaporation of the dark red suspension in vacuo, the residue is treated with water and made alkaline with ca 100 ml of 15 percent potassium carbonate solution. The separated material is filtered off under suction and washed with water. After recrystallisation from ca 500 ml of ethanol, there is obtained ethyl 8-fluoro-5,6-dihydro-6-oxo-4H-imidazo[1,5-a][1,4]benzodiazepine-3-carboxylate of melting point 298° C.

EXAMPLE 9

0.1 g (2 mmol) of sodium hydride (55 percent oil dispersion) are suspended in 10 ml of dry dimethylformamide and treated with 0.5 g (1.7 mmol) of ethyl 8-fluoro-5,6-dihydro-6-oxo-4H-imidazo[1,5-a][1,4]benzodiazepine-3-carboxylate. After completion of the gas evolution, 0.13 ml (2 mmol) of methyl iodide is added and the mixture is stirred at room temperature for 2 hours. The mixture is poured into ca 60 ml of water and extracted three times with 30 ml of chloroform each time. The combined chloroform extracts are washed with ca 30 ml of water, dried over magnesium sulphate and evaporated. After recrystallisation from ethyl acetate, there is obtained ethyl 8-fluoro-5,6-dihydro-5-methyl-6-oxo-4H-imidazo[1,5-a][1,4]benzodiazepine-3-carboxylate of melting point 196°–197° C.

EXAMPLE 10

(a) A mixture of 34.5 g (0.22 mol) of 6-fluoro-2-nitrotoluene, 30.7 g (0.22 mol) of potassium carbonate, 105.4 g (0.66 mol) of potassium permanganate and 3.3 liters of water is heated at 100° C. until the permanganate is decolorised (ca 2.5 hours). After cooling and removal of the unreacted 6-fluoro-2-nitrotoluene by extraction with ethyl acetate, the aqueous phase is adjusted to pH 1 with hydrochloric acid and extracted three times with ethyl acetate. The combined organic extracts are dried over magnesium sulphate and concentrated, there being obtained 6-fluoro-2-nitrobenzoic acid. After recrystallisation from ethyl acetate/n-hexane, the product melts at 146°–148° C.

(b) 2.7 g of 10 percent palladium/carbon are added to a solution of 20.0 g (0.108 mol) of 6-fluoro-nitrobenzoic acid in a mixture of 200 ml of methanol and 27 ml of concentrated hydrochloric acid and the resulting mixture is hydrogenated at 35°–40° C. under a slight overpressure. After filtration of the catalyst and concentration of the filtrate, the crude product is recrystallised from methanol/ether. There is obtained 6-fluoroanthranilic acid hydrochloride of melting point 176°–178° C. (decomposition).

(c) Phosgene is conducted at 35°–40° C. for 3 hours into a solution of 23 g (0.148 mol) of 6-fluoroanthranilic acid hydrochloride in a mixture of 300 ml of tetrahydrofuran and 150 ml of 4 N hydrochloric acid. After removal of the phosgene, the mixture is diluted with 500 ml of water and the precipitate is filtered off. There is obtained crude 6-fluoroisatoic acid anhydride of melting point 265°–267° C. (decomposition).

(d) 7.2 g (0.04 mol) of 6-fluoroisatoic acid anhydride and 3.9 g (0.044 mol) of sarcosine are added to 10 ml of dimethyl sulphoxide and the mixture is heated at 100° C. for 30 minutes. After cooling and diluting with 15 ml of water, the separated substance is filtered off. After drying, there is obtained 6-fluoro-3,4-dihydro-4-methyl-2H-1,4-benzodiazepine-2,5(1H)-dione of melting point 214°–217° C. (decomposition).

(e) 3.18 g (15.2 mmol) of 6-fluoro-3,4-dihydro-4-methyl-2H-1,4-benzodiazepine-2,5(1H)-dione in 20 ml of dimethylformamide are treated under an argon atmosphere with 0.59 g (15.2 mmol) of sodium hydride (60 percent oil dispersion) and stirred for 1 hour. The solution obtained is cooled to −30° C. and treated dropwise at this temperature with 2.63 g (15.2 mmol) of diethylchlorophosphate. The mixture is subsequently stirred at −20° C. for 10 minutes.

Separately, 1.79 g (16 mmol) of potassium tert.butylate are dissolved in 3 ml of dimethylformamide and treated at −40° C. to −50° C. with 1.18 g (16 mmol) of ethyl isocyanoacetate. The resulting orange coloured solution is added dropwise at −15° C. to the mixture obtained according to the preceding paragraph. The resulting mixture is stirred without cooling for 10 minutes, neutralised with 1.50 ml of acetic acid and the dark brown solution is poured into water. After three-fold extraction with 60 ml of chloroform each time, the combined chloroform phases are washed five times with 150 ml of water each time and evaporated. After recrystallisation of the crude product from ethyl acetate, there is obtained ethyl 7-fluoro-5,6-dihydro-5-methyl-6-oxo-4H-imidazo[1,5-a][1,4]benzodiazepine-3-carboxylate of melting point 196°–198.5° C.

EXAMPLE 11

(a) 7.2 g (0.04 mol) of 6-fluoroisatoic acid anhydride and 5 g (0.044) mol of (S)-3,4-dehydroproline are added to 10 ml of dimethyl sulphoxide and heated at 100° C. for 45 minutes. After cooling and diluting with 15 ml of water, the separated crystals are filtered off. After drying, there is obtained (S)-6-fluoro-3,11a-dihydro-5H-pyrrolo[2,1-c][1,4]benzodiazepine-5,11(10H)-dione of melting point 238°–240° C.

(b) A mixture of 4.64 g (20 mmol) of (S)-6-fluoro-3,11a-dihydro-5H-pyrrolo[2,1-c][1,4]benzodiazepine-5,11(10H)-dione and 25 ml of dimethylformamide is treated under argon with 0.80 g (22 mmol) of sodium hydride (60 percent oil dispersion) and stirred at a temperature between 0° C. and 10° C. for 1 hour. The solution obtained is cooled to −30° C. and treated with 3.79 g (22 mmol) of diethylchlorophosphate. The resulting mixture is stirred at −20° C. for 10 minutes.

Separately, a solution of 2.24 g (22 mmol) of potassium tert.butylate in 5 ml of dimethylformamide is treated in an acetone/dry-ice bath with 2.26 g (20 mmol) of ethyl isocyanoacetate. The solution obtained is added dropwise at −20° C. to −10° C. to the mixture obtained according to the preceding paragraph. The resulting mixture is stirred without cooling for 10 minutes, neutralised with 2 ml of acetic acid and poured into water. The mixture is extracted three times with 50 ml of chloroform each time, the combined organic phases are washed five times with 200 ml of water each time, dried over magnesium sulphate and the solvent is removed. After column chromatography of the crude product and subsequent recrystallisation from ethyl acetate, there is obtained ethyl 8-fluoro-11,13a-dihydro-9-oxo-9H-imidazo[1,5-a]pyrrolo[2,1-c][1,4]benzodiazepine-1-carboxylate of melting point 200°–201° C.

EXAMPLE 12

2.86 g (12.2 mol) of (S)-(+)-7-fluoro-1,2,3,11a-tetrahydro-5H-pyrrolo[2,1-c][1,4]benzodiazepine-5,11-(10H)-dione are placed in 15 ml of dry dimethylformamide and treated with 1.5 g (13.1 mmol) of potassium tert.butylate. The solution is stirred for 10 minutes and cooled to −30° C. At this temperature there are added dropwise 2.18 g (12.6 mmol) of diethylchlorophosphate and the mixture is stirred at −20° C. for 10 minutes.

Separately, 1.5 g (13.2 mmol) of potassium tert.butylate are dissolved in 5 ml of dimethylformamide, this solution is cooled to −50° C. and treated with 1.5 g (13.3 mmol) of ethyl isocyanoacetate. This solution is immediately added dropwise at −20° C. to −10° C. to the mixture obtained according to the preceding paragraph. The resulting mixture is stirred without cooling for 1 hour, neutralised with 1.2 ml of glacial acetic acid, poured into 300 ml of water and extracted three times with 100 ml of ethyl acetate each time. The combined organic extracts are washed five times with 200 ml of water each time, dried over magnesium sulphate and evaporated. The semicrystalline residue is recrystallised from 30 ml of ethyl acetate, there being obtained ethyl (S)-7-fluoro-11,12,13,13a-tetrahydro-9-oxo-9H-imidazo[1,5-a]pyrrolo[2,1-c][1,4]benzodiazepine-1-carboxylate of melting point 194°–195° C.

EXAMPLE 13

(a) 29.1 g (0.14 mol) of 6-chloroisatoic acid anhydride are stirred at 110° C. for 1 hour with 13.12 g (0.14 mol) of sarcosine in 150 ml of dimethyl sulphoxide. The solution obtained is concentrated and the residue is recrystallised from alcohol. There is obtained 6-chloro-3,4-dihydro-4-methyl-2H-1,4-benzodiazepine-2,5(1H)-dione of melting point 237°–238° C.

(b) A solution of 10 g (44.5 mmol) of 6-chloro-3,4-dihydro-4-methyl-2H-1,4-benzodiazepine-2,5(1H)-dione in 100 ml of dimethylformamide is treated under an argon atmosphere with 5.50 g (49 mmol) of potassium tert.butylate and stirred for 20 minutes. The solution obtained is cooled to −30° C. and at this temperature 3.45 g (49 mmol) of diethylchlorophosphate are added dropwise. The mixture is subsequently stirred at −20° C. for 10 minutes.

Meanwhile, a solution of 5.50 g (40 mmol) of potassium tert.butylate in 10 ml of dimethylformamide is cooled in an acetone/dry-ice bath and treated with 5.54 g (49 mmol) of ethyl isocyanoacetate. The dark red solution is added at −10° C. to −20° C. to the mixture obtained according to the preceding paragraph and the resulting mixture is stirred without cooling for 0.5 hour before it is neutralised with 5 ml of glacial acetic acid and poured into ca 300 ml of water. The orange coloured solution is extracted three times with chloroform. The organic phase is washed five times with water, dried over magnesium sulphate and evaporated. After chromatography and recrystallisation from ethyl acetate, there is obtained ethyl 7-chloro-5,6-dihydro-5-methyl-6-oxo-4H-imidazo[1,5-a][1,4]benzodiazepine-3-carboxylate of melting point 229°–230° C.

EXAMPLE 14

(a) 10 g (50.6 mmol) of 6-chloroisatoic acid anhydride are stirred at 110° C. for 2 hours with 5.82 g (50.6 mmol) of L-proline in 80 ml of dimethyl sulphoxide. The solution is evaporated and the residue is crystallised from ethyl acetate. There is obtained (S)-6-chloro-1,2,3,11a-tetrahydro-5H-pyrrolo[2,1-c][1,4]benzodiazepine-5,11(10H)-dione of melting point 264°–266° C.

(b) A solution of 4.0 g (16 mmol) of (S)-6-chloro-1,2,3,11a-tetrahydro-5H-pyrrolo[2,1-c][1,4]benzodiazepine-5,11(10)-dione in 30 ml of dimethylformamide is treated under an argon atmosphere with 0.57 g (16 mmol) of sodium hydride (60 percent oil dispersion) and stirred at room temperature for 1 hour. 3.02 g (17.5 mmol) of diethylchlorophosphate are added dropwise to the thus-obtained suspension at −20° C. and the mixture is stirred at this temperature for 10 minutes.

Separately, a solution of 1.96 g (17.5 mmol) of potassium tert.butylate in 5 ml of dimethylformamide is cooled in an acetone/dry-ice bath and treated with 1.92 g (17 mmol) of ethyl isocyanoacetate. This solution is added slowly at −10° C. to −20° C. to the mixture obtained according to the preceding paragraph. The resulting mixture is stirred without cooling for 0.5 hour, neutralised with 1.6 ml of acetic acid and poured into ca 200 ml of water. The orange coloured solution is extracted three times with chloroform. The organic phase is washed five times with water, dried over magnesium sulphate and evaporated. After chromatography and recrystallisation from ethyl acetate, there is obtained ethyl (S)-8-chloro-11,12,13,13a-tetrahydro-9-oxo-9H-imidazo[1,5-a]pyrrolo[2,1-c][1,4]benzodiazepine-1-carboxylate of melting point 182.5°–184° C.

EXAMPLE 15

(a) N-(2,4-dimethoxybenzyl)glycine is prepared by the reaction of glycine with 2,4-dimethoxybenzaldehyde in the presence of sodium hydroxide, reduction with palladium-on-carbon in methanol and subsequent neutralisation with 2 N hydrochloric acid. The aqueous solution obtained is concentrated. 41.9 g of this mixture of N-(2,4-dimethoxybenzyl)-glycine and sodium chloride are stirred at 110° C. for 1.5 hours in 300 ml of dimethyl sulphoxide with 23.18 g (142 mmol) of isatoic acid anhydride. The mixture is poured into ca 2 liters of water and stirred for 0.5 hour. The separated crystals are filtered off under suction, washed with water and dried. After recrystallisation from ethyl acetate, there is obtained 3,4-dihydro-4-(2,4-dimethoxybenzyl)-2H-1,4-benzodiazepine-2,5(1H)-dione of melting point 151°-152.5° C.

(b) A solution of 110 g (0.33 mol) of 3,4-dihydro-4-(2,4-dimethoxybenzyl)-2H-1,4-benzodiazepine-2,5(1H)-dione in 330 ml of dry dimethylformamide is treated with 45.74 g (0.40 mol) of potassium tert.butylate. The solution is cooled to −30° C., 61 g (0.35 mol) of diethylchlorophosphate are added dropwise at a temperature between −30° C. and −20° C. over a period of 20 minutes and the mixture is stirred at −20° C. for 10 minutes.

Separately, 41.6 g (0.37 mol) of potassium tert.butylate are dissolved in 90 ml of dimethylformamide, cooled to ca −50° C. and treated with 42 g (0.37 mol) of ethyl isocyanoacetate. The thus-obtained orange coloured solution is added dropwise at −20° C. to −10° C. to the mixture obtained according to the preceding paragraph. The resulting mixture is stirred for 0.5 hour, neutralised with 33 ml of acetic acid, poured into ca 1.7 liters of water and extracted three times with chloroform. The combined chloroform phases are washed five times with water, dried over magnesium sulphate and evaporated. After recrystallisation from ethyl acetate, there is obtained ethyl 5,6-dihydro-5-(2,4-dimethoxybenzyl)-6-oxo-4H-imidazo[1,5-a][1,4]benzodiazepine-3-carboxylate of melting point 136°-138° C.

(c) 90 g (214 mmol) of ethyl 5,6-dihydro-5-(2,4-dimethoxybenzyl)-6-oxo-4H-imidazo[1,5-a][1,4]benzodiazepine-3-carboxylate are heated to reflux while stirring for 3 hours in 300 ml of trifluoroacetic acid. After evaporation in vacuo, the residue is treated with water and made alkaline with 10 percent potassium carbonate solution. The separated material is filtered off under suction, washed with water and dried in vacuo. After recrystallisation from chloroform/hexane, there is obtained ethyl 5,6-dihydro-6-oxo-4H-imidazo[1,5-a][1,4]benzodiazepine-3-carboxylate of melting point 248°-250° C.

EXAMPLE 16

70 mg (1.6 mmol) of sodium hydride (55 percent oil dispersion) are suspended in 5 ml of dry dimethylformamide and treated with 135 mg (0.5 mmol) of ethyl 5,6-dihydro-6-oxo-4H-imidazo[1,5-a][1,4]benzodiazepine-3-carboxylate. After completion of the gas evolution, 0.15 ml (2.3 mmol) of methyl iodide is added and the mixture is stirred at room temperature for 1 hour. The mixture is poured into ca 50 ml of water, neutralised with glacial acetic acid and extracted three times with ca 30 ml of chloroform each time. The combined chloroform phases are washed with ca 20 ml of water, dried over magnesium sulphate and evaporated. After column chromatography and recrystallisation from ethyl acetate, there is obtained ethyl 5,6-dihydro-5-methyl-6-oxo-4H-imidazo[1,5-a][1,4]benzodiazepine-3-carboxylate of melting point 166°-167° C.

EXAMPLE 17

19.0 g (0.10 mol) of 3,4-dihydro-4-methyl-2H-1,4-benzodiazepine-2,5(1H)-dione are placed in 100 ml of dry dimethylformamide under an argon atmosphere. 15.5 g (0.12 mol) of potassium tert.butylate are added thereto, the temperature rising from 25° C. to 39° C. The mixture is cooled to room temperature and 18.2 g (0.105 mol) of diethylchlorophosphate are added dropwise at a temperature between 18° C. and 22° C.

Separately, 11.2 g (0.10 mol) of potassium tert.butylate are dissolved in 30 ml of dimethylformamide. This solution is cooled to ca −50° C. and treated under argon with 11.3 g (0.10 mol) of ethyl isocyanoacetate. Subsequently, this solution is added dropwise at 18°-23° C. while cooling to the mixture obtained according to the preceding paragraph. The resulting mixture is stirred at room temperature for 1 hour, 5 ml of acetic acid are added, the mixture is poured into 500 ml of water and extracted twice with 200 ml of chloroform each time. The combined chloroform extracts are washed three times with 300 ml of water each time, dried over magnesium sulphate and evaporated. 150 ml of ethyl acetate are added to the oily residue and it is left to crystallise at 0° C. The separated crystals are filtered off under suction and washed with cold ethyl acetate, there being obtained ethyl 5,6-dihydro-5-methyl-6-oxo-4H-imidazo[1,5-a][1,4]benzodiazepine-3-carboxylate of melting point 163°-165° C. After recrystallisation from 50 ml of ethyl acetate, the product melts at 164°-165° C.

EXAMPLE 18

(a) 21.5 g (75.4 mmol) of ethyl 5,6-dihydro-5-methyl-6-oxo-4H-imidazo[1,5-a][1,4]benzodiazepine-3-carboxylate are dissolved in 250 ml of hot absolute tetrahydrofuran (filtered over Alox basic I) under an argon atmosphere while stirring, cooled to ca 30° C. and treated dropwise with a solution of 1.66 g (75.4 mmol) of lithium borohydride in 25 ml of absolute tetrahydrofuran. The mixture is heated to boiling under reflux for 6 hours, cooled to room temperature and decomposed with 50 ml of 3 N aqueous hydrochloric acid. The mixture is stirred at 60° C. for a further 2 hours and the tetrahydrofuran is removed in vacuo. The residue is made alkaline with concentrated ammonia and left to stand in an ice-bath for 2 hours. The crude product is filtered off under suction, washed with a large amount of water and recrystallised from ethanol. There is obtained 4,5-dihydro-3-(hydroxymethyl)-5-methyl-6H-imidazo[1,5-a][1,4]benzodiazepin-6-one of melting point 224°-226° C.

(b) A mixture of 12.2 g (50 mmol) of 4,5-dihydro-3-(hydroxymethyl)-5-methyl-6H-imidazo[1,5-a][1,4]benzodiazepin-6-one, 80.0 g of manganese dioxide and 500 ml of absolute methylene chloride is stirred at room temperature for 1 hour under an argon atmosphere and subsequently the manganese dioxide is filtered off under suction over Dicalit while rinsing with methylene chloride. The filtrate is evaporated to dryness in vacuo. After warming the residue in ca 150 ml of ethyl acetate, there is obtained 5,6-dihydro-5-methyl-6-oxo-4H-imidazo[1,5-a][1,4]benzodiazepine-3-carboxaldehyde of melting point 205°-207° C.

(c) A solution of 10.6 g (37.3 mmol) of sodium carbonate decahydrate in 40 ml of water is added dropwise to a suspension of 7.2 g (29.8 mmol) of 5,6-dihydro-5-methyl-6-oxo-4H-imidazo[1,5-a][1,4]benzodiazepine-3-carboxaldehyde and 2.53 g (37.3 mmol) of hydroxylamine hydrochloride in 250 ml of water. The mixture is stirred at 70° C. for 6 hours and cooled to room temperature. The separated crude product is filtered off under suction, washed with water and recrystallised while still moist from ca 60 ml of dimethylformamide. There is thus obtained 5,6-dihydro-5-methyl-6-oxo-4H-imidazo[1,5-a][1,4]benzodiazepine-3-carboxaldehyde-3-oxime of melting point 268°–274° C. (decomposition).

(d) A solution of 4.8 g (18.7 mmol) of 5,6-dihydro-5-methyl-6-oxo-4H-imidazo[1,5-a][1,4]benzodiazepine-3-carboxaldehyde-3-oxime in 50 ml of acetic acid anhydride is heated to boiling under reflux for 28 hours. After evaporation of the mixture in vacuo, the residue is taken up in 150 ml of chloroform and washed twice with 30 ml of saturated sodium hydrogen carbonate solution each time and with 30 ml of water. The organic phase is dried over magnesium sulphate and evaporated. After column chromatography on silica gel and recrystallisation from ethyl acetate, there is obtained 5,6-dihydro-5-methyl-6-oxo-4H-imidazo[1,5-a][1,4]benzodiazepine-3-carbonitrile of melting point 184°–186° C.

EXAMPLE 19

(a) 1.22 g (50.2 mmol) of magnesium shavings are covered with 60 ml of absolute diethyl ether under an argon atmosphere and treated with 2–3 drops of ethyl iodide. When the Grignard reaction starts, a solution of 4.3 ml (51 mmol) of ethyl iodide in 10 ml of absolute diethyl ether is added dropwise at the boiling point. After the magnesium has dissolved completely, the mixture is treated dropwise with a solution, warmed to 30° C., of 0.65 g (40 mmol) of 5,6-dihydro-5-methyl-6-oxo-4H-imidazo[1,5-a][1,4]benzodiazepine-3-carboxaldehyde in 200 ml of absolute tetrahydrofuran. The yellow coloured suspension is heated to boiling under reflux for ca 5.5 hours, cooled to room temperature and poured into 600 ml of ice/water. The mixture is filtered over Dicalit while rinsing with tetrahydrofuran. After concentration of the filtrate in vacuo, the residue is taken up in 250 ml of chloroform. The chloroform phase is washed twice with 60 ml of water each time, dried over magnesium sulphate and concentrated. The crude product is chromatographed on silica gel using chloroform/methanol (19:1, vol/vol) for the elution. After recrystallisation from ca 40 ml of ethyl acetate, there is obtained 4,5-dihydro-3-(1-hydroxypropyl)-5-methyl-6H-imidazo[1,5-a][1,4]benzodiazepin-6-one of melting point 145°–147° C.

(b) A mixture of 1.84 g (6.8 mmol) of 4,5-dihydro-3-(1-hydroxypropyl)-5-methyl-6H-imidazo[1,5-a][1,4]benzodiazepin-6-one, 16 g of manganese dioxide and 150 ml of methylene chloride is stirred at room temperature under an argon atmosphere for 2 hours. The manganese dioxide is filtered off under suction over a glass filter and the filtrate is evaporated in vacuo. After recrystallisation of the residue from 100 ml of ethyl acetate, there is obtained 4,5-dihydro-5-methyl-3-propionyl-6H-imidazo[1,5-a][1,4]-benzodiazepin-6-one of melting point 215°–216° C.

EXAMPLE 20

(a) A mixture of 910 ml of diethyl malonate and 3.0 liters of tetrahydrofuran is cooled to 0° C. while stirring under argon and treated portionwise with 350 g of sodium hydride (55 percent oil dispersion) in such a manner that the temperature does not exceed 15° C. Thereafter, the mixture is stirred at room temperature overnight, cooled to 0°–5° C. and 290 ml of diethylchlorophosphate are added dropwise over a period of 15 minutes. After a further 2 hours at room temperature, the mixture is treated slowly with a suspension, warmed to ca 45° C., of 190 g of 4-methyl-3H-1,4-benzodiazepine-2,5(1H,4H)-dione in 2 liters of tetrahydrofuran, the addition taking ca 1 hour. The mixture is stirred at room temperature overnight, cooled to 5° C. and treated dropwise with 350 ml of glacial acetic acid. There is thus obtained a thick slurry which is again made well stirrable by the addition of 500 ml of water. The tetrahydrofuran is distilled off from the mixture and the partially crystalline residue is partitioned between ether and water. The organic phase is washed with water, dried and concentrated. The red-brown coloured residue is dissolved in 2 liters of boiling n-hexane and then cooled. The mixture is left to stand at 2° C. overnight and the resulting crystallisate is filtered off under suction. The light yellow crystals are subsequently dissolved in 800 ml of hot toluene and crystallised by the addition of 600 ml of n-hexane and scratching. After standing in the cold overnight, the crystals are filtered off under suction and dried at 50° C. in vacuo. There is obtained diethyl(1,3,4,5-tetrahydro-4-methyl-5-oxo-2H-1,4-benzodiazepin-2-ylidene)malonate in the form of white crystals of melting point 139° C.

(b) A mixture of 33.2 g (0.1 mol) of diethyl(1,3,4,5-tetrahydro-4-methyl-5-oxo-2H-1,4-benzodiazepin-2-ylidene)malonate, 8.0 g (0.2 mol) of sodium hydroxide and 400 ml of absolute ethanol is heated to reflux for 3 hours. The mixture is subsequently left to crystallise at 0° C. and the separated solid material is filtered off under suction and transferred to a separating funnel. 100 ml of chloroform and 25 ml of water are added thereto. Then, the aqueous phase is separated. The organic phase is washed with 25 ml of water, dried over sodium sulphate and evaporated. There is obtained crystalline ethyl(1,3,4,5-tetrahydro-4-methyl-5-oxo-2H-1,4-benzodiazepin-2-ylidene)acetate of melting point 154°–155° C.

(c) 32.2 g (0.124 mol) of ethyl(1,3,4,5-tetrahydro-4-methyl-5-oxo-2H-1,4-benzodiazepin-2-ylidene)acetate are dissolved in 300 ml of acetic acid and treated at room temperature with 12.8 g (0.186 mol) of sodium nitrite. The mixture is stirred at room temperature for a further 10 minutes, then poured into 1 liter of water and extracted three times with 200 ml of chloroform each time. The combined chloroform phases are washed with 100 ml of water, dried over magnesium sulphate and evaporated. The residue is recrystallised from ethyl acetate. There is obtained ethyl 4,5-dihydro-4-methyl-5-oxo-3H-1,4-benzodiazepine-2-glyoxylate α-oxime of melting point 173°–174° C.

(d) 4.34 g (15 mmol) of ethyl 4,5-dihydro-4-methyl-5-oxo-3H-1,4-benzodiazepine-2-glyoxylate α-oxime are dissolved in 60 ml of tetrahydrofuran, treated with 30 ml of ethanol and 1.0 g of 5% palladium-on-carbon and hydrogenated at normal pressure and room temperature. After uptake of the theoretical amount of hydrogen (1 hour), the catalyst is filtered off and the filtrate is evaporated in vacuo. There is thus obtained ethyl α-amino-1,3,4,5-tetrahydro-5-oxo-2H-1,4-benzodiazepin-2-ylidene-acetate in the form of a pale yellow oil which is sensitive to oxidation.

(e) 4.1 g of ethyl α-amino-1,3,4,5-tetrahydro-5-oxo-2H-1,4-benzodiazepin-2-ylidene-acetate are dissolved in 25 ml of ethyl acetate, treated with 3.1 ml (18.1 mmol) of N,N-dimethylformamide diethyl acetal and heated to boiling under reflux for 0.5 hour. After cooling, the separated material is filtered off under suction and recrystallised from ethanol. After chromatography of the mother liquor, there is obtained a second portion of ethyl 5,6-dihydro-5-methyl-6-oxo-4H-imidazo[1,5-a][1,4]benzodiazepine-3-carboxylate of the same purity; melting point 166°–168° C.

EXAMPLE 21

1.10 g of ethyl α-amino-1,3,4,5-tetrahydro-4-methyl-5-oxo-2H-1,4-benzodiazepin-2-ylidene-acetate are dissolved in 15 ml of toluene and treated with 1.0 ml of triethyl orthoformate. The mixture is heated to reflux for 50 minutes, subsequently cooled and evaporated in vacuo. The crystalline residue is suspended in 25 ml of ethyl acetate, filtered off and dried. There is obtained ethyl 5,6-dihydro-5-methyl-6-oxo-4H-imidazo[1,5-a][1,4]benzodiazepine-3-carboxylate of melting point 165° C.

EXAMPLE 22

(a) 1.10 g of ethyl α-amino-1,3,4,5-tetrahydro-4-methyl-5-oxo-2H-1,4-benzodiazepin-2-ylidene-acetate are dissolved in 20 ml of methylene chloride, treated with 0.65 ml of 37 percent aqueous formaldehyde solution and stirred at room temperature for 30 minutes. The mixture is washed three times with 10 ml of water each time. The organic phase is separated, dried and evaporated in vacuo. The residue is dissolved in ethyl acetate and decolourised with active carbon. After filtration of the carbon and concentration of the filtrate, a light yellow oil is obtained.

(b) The foregoing oil is dissolved in 10 ml of methylene chloride and stirred at room temperature for 30 minutes together with 3.5 g of manganese dioxide. After filtration of the suspension while rinsing with methylene chloride, the filtrate is evaporated in vacuo. There is obtained a yellow coloured oil which, after the addition of ethyl acetate and ether, yields crystalline ethyl 5,6-dihydro-5-methyl-6-oxo-4H-imidazo[1,5-a][1,4]benzodiazepine-3-carboxylate of melting point 162°–164° C.

EXAMPLE 23

1.0 g of ethyl α-amino-1,3,4,5-tetrahydro-4-methyl-5-oxo-2H-1,4-benzodiazepin-2-ylidene-acetate are dissolved in 20 ml of methylene chloride, treated with 0.65 ml of 37 percent aqueous formaldehyde solution and stirred in the presence of air at room temperature for 2 hours. The solution is subsequently washed twice with 10 ml of water each time. The organic phase is separated, dried and decolourised with active carbon. After filtration of the carbon, the filtrate is evaporated in vacuo and the residue is chromatographed on 20 g of silica gel. Elution is carried out firstly with chloroform and subsequently with chloroform/ethanol (985:15). The fractions which contain ethyl 5,6-dihydro-5-methyl-6-oxo-4H-imidazo[1,5-a][1,4]benzodiazepine-3-carboxylate as the main component are combined and evaporated in vacuo. The residue is dissolved in ethanol and crystallised by the addition of diisopropyl ether. There is obtained ethyl 5,6-dihydro-5-methyl-6-oxo-4H-imidazo[1,5-a][1,4]benzodiazepine-3-carboxylate of melting point 162°–164° C.

EXAMPLE 24

285 mg (1 mmol) of ethyl 5,6-dihydro-5-methyl-6-oxo-4H-imidazo[1,5-a][1,4]benzodiazepine-3-carboxylate and 66 mg of potassium cyanide are heated to boiling under reflux for 24 hours in 10 ml of methanol. Then, the mixture is concentrated on a rotary evaporator, the residue is partitioned between water and chloroform, extracted twice with chloroform, the chloroform phase is dried over magnesium sulphate and evaporated. There is obtained methyl 5,6-dihydro-5-methyl-6-oxo-4H-imidazo[1,5-a][1,4]benzodiazepine-3-carboxylate of melting point 212°–214° C. This product is uniform according to thin-layer chromatography.

EXAMPLE 25

285 mg (1 mmol) of ethyl 5,6-dihydro-5-methyl-6-oxo-4H-imidazo[1,5-a][1,4]benzodiazepine-3-carboxylate and 50 mg of potassium cyanide are stirred at 60° C. for 72 hours in 10 ml of 2-propanol. Then, the mixture is concentrated on a rotary evaporator, the residue is partitioned between water and chloroform, extracted twice with chloroform, the chloroform phase is dried over magnesium sulphate and evaporated. There is obtained isopropyl 5,6-dihydro-5-methyl-6-oxo-4H-imidazo[1,5-a][1,4]benzodiazepine 3-carboxylate of melting point 190°–192° C. This product is uniform according to thin-layer chromatography.

EXAMPLE 26

A mixture of 1.42 g (5 mmol) of ethyl 5,6-dihydro-5-methyl-6-oxo-4H-imidazo[1,5-a][1,4]benzodiazepine-3-carboxylate, 100 mg of potassium cyanide and 10 ml of ethyleneglycol is stirred at 130° C. for 6 hours, subsequently diluted with chloroform, washed with water, dried over magnesium sulphate and evaporated. After recrystallisation of the residue from ethyl acetate, there is obtained 2-hydroxyethyl-5,6-dihydro-5-methyl-6-oxo-4H-imidazo[1,5-a][1,4]benzodiazepine-3-carboxylate of melting point 222°–223° C.

EXAMPLE 27

670 mg (2.3 mmol) of ethyl 5,6-dihydro-5-methyl-6-oxo-4-H-imidazo[1,5-a][1,4]benzodiazepine-3-carboxylate and 497 mg (1.23 mmol) of 2,4-bis(p-methoxyphenyl)-1,3,2,4-dithiadiphosphetane-2,4-disulphide are heated to boiling under reflux for 2.5 hours in 5 ml of absolute toluene. The mixture is chromatographed on silica gel with ethyl acetate and there is obtained ethyl 5,6-dihydro-5-methyl-6-thioxo-4H-imidazo[1,5-a][1,4]benzodiazepine-3-carboxylate of melting point 164°–165° C.

EXAMPLE 28

(a) A mixture of 14.0 g (79 mmol) of 6-methylisatoic acid anhydride, 7.04 g (79 mmol) of sarcosine and 80 ml of dimethyl sulphoxide is stirred at 110° C. for 3 hours. The red coloured solution is evaporated in a high vacuum. The residue is treated with 80 ml of ethanol, the product crystallising out. There is obtained 3,4-dihydro-4,6-dimethyl-2H-1,4-benzodiazepine-2,5(1H)-dione of melting point 200°–202° C.

(b) A solution of 9 g (44 mmol) of 3,4-dihydro-4,6-dimethyl-2H-1,4-benzodiazepine-2,5(1H)-dione in 100 ml of dimethylformamide is treated with 1.69 g of sodium hydride (60 percent oil dispersion) and stirred for 1 hour. The thus-obtained suspension is treated dropwise at −20° C. with 7.59 g (44 mmol) of diethylchlorophosphate. Subsequently, the mixture is stirred at this temperature for a further 10 minutes.

Separately, a solution of 5.60 g (50 mmol) of potassium tert.butylate in 10 ml of dimethylformamide is cooled in an acetone/dry-ice bath and treated with 5.65 g (50 mmol) of ethyl isocyanoacetate. This solution is added dropwise at −10° C. to −20° C. to the mixture obtained according to the preceding paragraph. The resulting mixture is stirred without cooling for a further 0.5 hour, neutralised with 5 ml of acetic acid and poured into ca 300 ml of water. The orange coloured solution is extracted three times with chloroform. The organic phase is washed five times with water, dried over magnesium sulphate and evaporated. After recrystallisation of the residue from alcohol and ether, there is obtained ethyl 5,6-dihydro-5,7-dimethyl-6-oxo-4H-imidazo[1,5-a][1,4]benzodiazepine-3-carboxylate of melting point 146°–147° C.

EXAMPLE 29

(a) A solution of 13.6 g (0.0768 mol) of 6-methylisatoic acid anhydride and 8.8 g (0.0768 mol) of L-proline is heated at 110° C. for 1 hour in 75 ml of dimethyl sulphoxide. Subsequently, the mixture is evaporated to dryness in a high vacuum and the residue is recrystallised from ethyl acetate with the addition of active carbon. There is obtained (S)-1,2,3,11a-tetrahydro-6-methyl-5H-pyrrolo[2,1-c][1,4]benzodiazepine-5,11-(10H)-dione of melting point 212°–214° C.

(b) A solution of 5.76 g (25 mmol) of (S)-1,2,3,11a-tetrahydro-6-methyl-5H-pyrrolo[2,1-c][1,4]benzodiazepine-5,11(10H)-dione in 40 ml of dimethylformamide is treated under an argon atmosphere with 0.9 g (25 mmol) of sodium hydride (60 percent oil dispersion) and stirred for 1 hour. 4.23 g (25 mmol) of diethylchlorophosphate are added dropwise at −20° C. to the solution obtained and the mixture is stirred at this temperature for 10 minutes.

Separately, a solution of 2.80 g (25 mmol) of potassium tert.butylate in 7 ml of dimethylformamide is cooled in an acetone/dry-ice bath and treated with 2.32 g (25 mmol) of ethyl isocyanoacetate. This solution is added dropwise at −10° C. to −20° C. to the mixture obtained according to the preceding paragraph. Subsequently, the cooling bath is removed, the mixture is stirred for 0.5 hour, neutralised with 2.5 ml of acetic acid and poured into ca 250 ml of water. The orange coloured solution is extracted three times with chloroform, the organic phase is washed five times with water, dried over magnesium sulphate and evaporated. After column chromatography and recrystallisation from ethyl acetate/hexane, there is obtained ethyl (S)-11,12,13,13a-tetrahydro-8-methyl-9-oxo-9H-imidazo[1,5-a]pyrrolo[2,1-c]benzodiazepine-1-carboxylate of melting point 152°–153° C.

EXAMPLE 30

A solution of 21.6 g (0.10 mol) of (S)-(+)-1,2,3,11a-tetrahydro-5H-pyrrolo[2,1-c][1,4]benzodiazepine-5,11(10H)-dione in 100 ml of dry dimethylformamide is treated under an argon atmosphere with 13.5 g (0.12 mol) of potassium tert.butylate, the temperature rising from 24° C. to 46° C. The mixture is cooled to room temperature and 18.2 g (0.105 mol) of diethylchlorophosphate are added dropwise at a temperature between 18° C. and 23° C.

Separately, 11.2 g (0.10 mol) of potassium tert.butylate are dissolved in 30 ml of dimethylformamide. This solution is cooled to ca −50° C. and treated under argon with 11.3 g (0.10 mol) of ethyl isocyanoacetate. Subsequently, this solution is added dropwise at 18°—23° C. while cooling to the mixture obtained according to the preceding paragraph. The resulting mixture is stirred at room temperature for 1 hour, 5 ml of acetic acid are added thereto, then the mixture is poured into 500 ml of water and extracted twice with 200 ml of chloroform each time. The combined chloroform phases are washed three times with 300 ml of water each time, dried over magnesium sulphate and evaporated. 150 ml of acetic acid are added to the oily residue and it is left to crystallise at 0° C. The separated crystals are filtered off under suction and washed with cold ethyl acetate, there being obtained ethyl (S)-11,12,13,13a-tetrahydro-9-oxo-9H-imidazo[1,5-a]pyrrolo[2,1-c][1,4]benzodiazepine-1-carboxylate of melting point 196°–197° C. The mother liquor is evaporated and the residue is dissolved in 50 ml of ethyl acetate. A further portion of the foregoing product (melting point 195°–196° C.) crystallises from the solution.

EXAMPLE 31

A mixture of 311 mg (1 mmol) of ethyl (S)-11,12,13,13a-tetrahydro-9-oxo-9H-imidazo[1,5-a]pyrrolo[2,1-c][1,4]benzodiazepine-1-carboxylate, 66 mg of potassium cyanide and 10 ml of absolute methanol is heated to boiling under reflux for 6 hours. The mixture is concentrated, a small amount of water is added, the mixture is extracted three times with 10 ml of chloroform each time, dried over magnesium sulphate, evaporated and recrystallised from ethyl acetate/hexane. There is obtained methyl (S)-11,12,13,13a-tetrahydro-9-oxo-9H-imidazo[1,5-a]pyrrolo[2,1-c][1,4]benzodiazepine-1-carboxylate of melting point 165°–167° C.

EXAMPLE 32

A mixture of 5.0 g (0.0161 mol) of ethyl (S)-11,12,13,13a-tetrahydro-9-oxo-9H-imidazo[1,5-a]pyrrolo[2,1-c][1,4]benzodiazepine-1-carboxylate and 3.46 g (0.0086 mol) of 2,4-bis(p-methoxyphenyl)-1,3,2,4-dithiadiphosphetane-2,4-disulphide is heated to boiling under reflux for 1.5 hours with 30 ml of toluene. This solution is chromatographed on silica gel using ethyl acetate for the elution. There is obtained ethyl (S)-11,12,13,13a-tetrahydro-9-thioxo-9H-imidazo[1,5-a]pyrrolo[2,1-c][1,4]benzodiazepine-1-carboxylate which is recrystallised from 180 ml of ethyl acetate and then melts at 227°–229° C.

EXAMPLE 33

934 mg (3 mmol) of ethyl (S)-11,12,13,13a-tetrahydro-9-oxo-9H-imidazo[1,5-a]pyrrolo[2,1-c][1,4-benzodiazepine-1-carboxylate are stirred at 60° C. for 48 hours with 198 mg (3 mmol) of potassium cyanide in 30 ml of dry 2-propanol. The mixture is evaporated in vacuo. The residue is treated with 30 ml of 2-propanol and 198 mg (3 mmol) of potassium cyanide and heated to boiling under reflux for 22 hours. After evaporation in vacuo, the residue is treated with water and extracted three times with 30 ml of chloroform each time. The combined chloroform phases are washed three times with 20 ml of water each time, dried over magnesium sulphate and evaporated. After recrystallisation from ethyl acetate/n-hexane, there is obtained isopropyl (S)-11,12,13,13a-tetrahydro-9-oxo-9H-imidazo[1,5-a]pyrrolo[2,1-c][1,4]benzodiazepine-1-carboxylate of melting point 207°–208° C.

EXAMPLE 34

(a) A mixture of 175 g (0.93 mol) of methyl 3-amino-2-thiophenecarboxylate hydrochloride, 1.8 liters of n-butanol and 77 g of sodium hydroxide is heated to boiling under reflux for 30 minutes. After concentration of the resulting suspension on a rotary evaporator, the mixture of sodium 3-amino-2-thiophenecarboxylate and sodium chloride is used directly in the next step. For this purpose, the mixture is treated with 800 ml of water, 280 ml of concentrated hydrochloric acid and 230 ml of tetrahydrofuran. Phosgene is conducted through this mixture at 15°–25° C. for 2.5 hours and then air is conducted through for 15 minutes. The separated solid material is filtered off under suction, washed with water and dried. There is obtained 2H-thieno[3,2-d][1,3]oxazine-2,4[1H]-dione of melting point 220°–221° C.

(b) A solution of 34.3 g (202 mmol) of 2H-thieno[3,2-d][1,3-oxazine-2,4(1H)-dione and 23.3 g (202 mmol) of L-proline is stirred at 110° C. for 1 hour in 200 ml of dimethyl sulphoxide. The brown coloured solution obtained is poured into 2 liters of water and stirred at room temperature overnight. The separated product is filtered off under suction, dried on a rotary evaporator and washed with ca 200 ml of boiling ethyl acetate. There is thus obtained (S)-5a,6,7,8-tetrahydro-5H-pyrrolo[1,2-a]thieno[3,2-e][1,4]diazepine-5,10(4)-dione of melting point 244°–247° C.

(c) 7 g (31.5 mmol) of (S)-5a,6,7,8-tetrahydro-5H-pyrrolo[1,2-a]thieno[3,2-e][diazepine-5,10(4)-dione are suspended in 30 ml of dimethylformamide under an argon atmosphere and treated at −50° C. with 3.92 g (35 mmol) of potassium tert.butylate. The solution is stirred for 10 minutes at −50° C., 6.0 g (35 mmol) of diethylchlorophosphate are added dropwise at this temperature and the mixture is stirred for 0.5 hour.

Separately, 3.92 g (35 mmol) of potassium tert.butylate, dissolved in 7 ml of dimethylformamide, are cooled in an acetone/dry-ice bath and treated with 3.95 g (35 mmol) of ethyl isocyanoacetate. The orange coloured solution obtained is added dropwise at −50° C. to the mixture obtained according to the preceding paragraph. Subsequently, the mixture is stirred at −50° C. to −60° C. for a further 10 minutes, neutralised with 3.2 ml of acetic acid and poured into ca 250 ml of water. The mixture is extracted twice with 200 ml of chloroform each time, the combined chloroform phases are washed five times with 300 ml of water each time, dried over magnesium sulphate and evaporated. After column chromatography and recrystallisation from ethyl acetate, there is obtained ethyl (S)-10,11,12,12a-tetrahydro-8-oxo-8H-imidazo[5,1-c]pyrrolo[1,2-a]thieno[3,2-e][1,4]diazepine-1-carboxylate of melting point 212.5°–213° C.

EXAMPLE 35

1.50 g of ethyl (S)-10,11,12,12a-tetrahydro-8-oxo-8H-imidazo[5,1-c]pyrrolo[1,2-a]thieno[3,2-e][1,4-diazepine-1-carboxylate are stirred at 50° C. for 20 hours together with 100 g of powdered potassium cyanide in 10 ml of methanol. The solution is concentrated and the residue is taken up in chloroform. The insoluble material is filtered off under suction and the filtrate is evaporated. After recrystallisation of the residue from chloroform/hexane, there is obtained methyl (S)-10,11,12,12a-tetrahydro-8-oxo-8H-imidazo[5,1-c]pyrrolo[1,2-a]thieno[3,2-e][1,4]diazepine-1-carboxylate of melting point 192°–193° C.

EXAMPLE 36

(a) A mixture of 30.0 g (177 mmol) of 2H-thieno[3,2-d][1,3]oxazine-2,4(1H)-dione and 17.3 g (195 mmol) of sarcosine in 100 ml of dimethyl sulphoxide is stirred at 110° C. for 1.5 hours. The dark brown coloured solution is poured into ca 600 ml of ice/water. The separated oil is taken up in ca 200 ml of ethyl acetate and the aqueous phase is evaporated in vacuo until crystallisation begins. The mixture is cooled in an ice-bath for ca 3 hours and the separated material is filtered off under suction and washed with a small amount of water. After drying on a rotary evaporator, there is obtained 3,4-dihydro-4-methyl-2H-thieno[3,2-e][1,4]diazepine-2,5(1H)-dione of melting point 270°–272° C.

(b) A suspension, cooled to 15° C., of 4.8 g (24.5 mmol) of 3,4-dihydro-4-methyl-2H-thieno[3,2-e][1,4]diazepine-2,5(1H)-dione in 30 ml of dimethylformamide is treated under an argon atmosphere with 3.28 g (29.4 mmol) of potassium tert.butylate. After cooling the dark brown coloured solution to −40° C., 3.7 ml (25.7 mmol) of diethylchlorophosphate are added dropwise at −40° C. to −30° C. The cooling bath is removed and the mixture is stirred for 20 minutes, the temperature rising to −15° C.

Separately, 3.0 g (27 mmol) of potassium tert.butylate are dissolved in 8 ml of dimethylformamide, cooled in an acetone/dry-ice bath and treated with 3.1 ml (27 mmol) of ethyl isocyanoacetate. The orange coloured solution is added dropwise at −15° C. to −10° C. to the mixture obtained according to the preceding paragraph. After removal of the cooling bath, the mixture is stirred until the temperature has risen to 20° C. Subsequently, the mixture is neutralised with 2 ml of acetic acid, poured into ca 150 ml of water and extracted three times with 150 ml of chloroform each time. The combined chloroform phases are washed three times with 100 ml of saturated sodium chloride solution each time, dried over magnesium sulphate and evaporated in vacuo. After column chromatography and recrystallisation from ethyl acetate/n-hexane, there is obtained ethyl 5,6-dihydro-5-methyl-6-oxo-4H-imidazo[1,5-a]thieno[2,3-f][1,4]diazepine-3-carboxylate of melting point 160°–162° C.

EXAMPLE 37

A suspension of 430 mg (1.5 mmol) of ethyl 5,6-dihydro-5-methyl-6-oxo-4H-imidazo[1,5-a]thieno[2,3-f][1,4]diazepine-3-carboxylate and 99 mg (1.5 mmol) of potassium cyanide in 15 ml of absolute methanol is heated under reflux for 3 hours while stirring. After evaporation in vacuo, the residue is treated with ca 20 ml of ice/water and extracted three times with ca 30 ml of chloroform each time. The combined chloroform phases are washed twice with ca 20 ml of water each time, dried over magnesium sulphate and evaporated. After washing with boiling ethyl acetate, there is obtained methyl 5,6-dihydro-5-methyl-6-oxo-4H-imidazo[1,5-a]thieno[2,3-f][1,4diazepine-3-carboxylate of melting point 244°–245° C.

EXAMPLE 38

A solution of 16.85 g (0.075 mol) of 3,4-dihydro-7-chloro-4-methyl-2H-1,4-benzodiazepine-2,5(1H)-dione in 150 ml of tetrahydrofuran is treated under an argon atmosphere with 8.98 g (0.08 mol) of potassium tert.butylate, cooled to −10° C., 12.94 g (0.08 mol) of diethylchlorophosphate are added dropwise and the mixture is stirred at −10° C. for 20 minutes.

Separately, 8.98 g (0.08 mol) of potassium tert.butylate are dissolved in 30 ml of dimethylformamide. This solution is treated under argon at ca −50° C. with 9.05 g (0.08 mol) of ethyl isocyanoacetate. Subsequently, this solution is added dropwise to the mixture obtained according to the preceding paragraph. The resulting mixture is stirred at room temperature for 1 hour, 5 ml of acetic acid are added, the mixture is poured into 500 ml of water and extracted three times with 200 ml of chloroform each time. The combined chloroform extracts are washed twice with 200 ml of water each time, dried over magnesium sulphate and evaporated. 75 ml of ethyl acetate are added to the residue and it is left to crystallise at 0° C. The separated crystals are filtered off under suction, washed with cold ethyl acetate and recrystallised from 125 ml of ethyl acetate. There is thus obtained ethyl 8-chloro-5,6-dihydro-5-methyl-6-oxo-4H-imidazo[1,5-a][1,4]benzodiazepine-3-carboxylate of melting point 188°–189° C.

EXAMPLE 39

A solution of 35 g (0.14 mol) of (S)-(+)-7-chloro-1,2,3,11a-tetrahydro-5H-pyrrolo[2,1-c][1,4]benzodiazepine-5,11(10H)-dione in 170 ml of dry dimethylformamide is treated under an argon atmosphere with 17.3 g (0.15 mol) of potassium tert.butylate, the temperature rising from 24° C. to 40° C. The mixture is cooled to −30° C. and 25 g (0.15 mol) of diethylchlorophosphate are added dropwise at a temperature between −30° C. and −20° C.

Separately, 16.8 g (0.15 mol) of potassium tert.butylate are dissolved in 50 ml of dimethylformamide. This solution is cooled to ca −50° C. and treated under argon with 17.42 g (0.15 mol) of ethyl isocyanoacetate. Subsequently, this solution is added dropwise at −20° C. to −10° C. to the mixture obtained according to the preceding paragraph. The resulting mixture is stirred without cooling for 1 hour, 14 ml of acetic acid are added, the mixture is subsequently poured into ca 1000 ml of water and extracted three times with 250 ml of chloroform each time. The combined chloroform phases are washed five times with 300 ml of water each time, dried over magnesium sulphate and evaporated. The residue is recrystallised from 500 ml of ethyl acetate. There is obtained ethyl (S)-(+)-7-chloro-11,12,13,13a-tetrahydro-9-oxo-9H-imidazo[1,5-a]pyrrolo[2,1-c][1,4]benzodiazepine-1-carboxylate of melting point 242°–244° C.

EXAMPLE 40

(a) A solution of 39.5 g of 5-bromoisatoic acid anhydride and 14.5 g of sarcosine in 150 ml of dimethyl sulphoxide is heated to 100° C. while stirring. In so doing, a vigorous evolution of carbon dioxide occurs from 70° C. and this has finished after ca 30 minutes. The mixture is stirred at 100° C. for a further 30 minutes and thereafter the mixture is poured into 900 ml of ice-water (temperature 5° C.) and the separated material is filtered off under suction. The crystals are washed with water and subsequently dried at 50° C. over phosphorus pentoxide in a vacuum drying cabinet. There is obtained 7-bromo-3,4-dihydro-4-methyl-2H-1,4-benzodiazepine-2,5(1H)-dione in the form of light beige crystals. A sample recrystallised from methanol has a melting point of 260°–261° C.

(b) A solution of 17 g (63 mmol) of 7-bromo-3,4-dihydro-4-methyl-2H-1,4-benzodiazepine-2,5(1H)-dione in 100 ml of dimethylformamide is treated under an argon atmosphere with 7.5 g (67 mmol) of potassium tert.butylate. The solution obtained is treated dropwise at −30° C. with 11.56 g (67 mmol) of diethylchlorophosphate and the mixture is stirred at −20° C. for 10 minutes.

Separately, a solution of 7.5 g (67 mmol) of potassium tert.butylate in 30 ml of dimethylformamide is cooled in an acetone/dry-ice bath and treated with 7.58 g (67 mmol) of ethyl isocyanoacetate. This solution is added at −10° C. to −20° C. to the mixture obtained according to the preceding paragraph. The cooling bath is removed, the mixture is stirred for 0.5 hour, neutralised with 8 ml of acetic acid and poured into ca 600 ml of water. The orange coloured solution is extracted three times with chloroform. The organic phase is washed five times with water, dried over magnesium sulphate and evaporated. After recrystallisation from ethyl acetate, there is obtained 8-bromo-5,6-dihydro-5-methyl-6-oxo-4H-imidazo[1,5-a][1,4]benzodiazepine-3-carboxylate of melting point 194°–195° C.

EXAMPLE 41

(a) A suspension of 12.2 g (0.063 mol) of 3-carbomethoxy-4-aminothiophene hydrochloride in 100 ml of methylene chloride is treated with 10 ml (0.126 mol) of chloroacetyl chloride and subsequently dropwise with 17.6 ml (0.126 mol) of triethylamine, the temperature being held below 25° C. The solution is poured into water and extracted twice with 50 ml of methylene chloride each time. The combined methylene chloride extracts are washed three times with 50 ml of water each time, dried over magnesium sulphate and evaporated. After chromatography on silica gel using methylene chloride for the elution, there is obtained crystalline 3-carbomethoxy-4-[(chloroacetyl)amino]thiophene of melting point 98°–100° C.

(b) A solution of 13.25 g (0.057 mol) of 3-carbomethoxy-4-[(chloroacetyl)amino]thiophene in a mixture of 60 ml of dimethylformamide and 60 ml of toluene is treated with 15.7 g of potassium carbonate and 0.05 g of potassium iodide and the mixture is warmed at 50° C. with constant introdution of methylamine. After 1 hour, the mixture is poured into ice/water and extracted three times with toluene. The combined toluene phases are washed twice with water, dried over magnesium sulphate and evaporated. The crude product is chromatographed on silica gel using chloroform for the elution. There is thus obtained 3-carbomethoxy-4-[[(methylamino)acetyl]amino]thiophene in the form of an oil. The corresponding hydrochloride melts at 234°–236° C. (decomposition).

(c) 9.5 g (0.036 mol) of 3-carbomethoxy-4-[[(methylamino)acetyl]amino]thiophene are heated at 250° C. in 2 g portions for 5 minutes under a protective gas and while stirring. The crude products from the various batches are washed together with methanol and concentrated. After repeated fractional crystallisation from dimethylformamide/ether, there is obtained pure 3,4-dihydro-4-methyl-5H-thieno[3,4-e][1,4]diazepine-2,5(1H)-dione of melting point 263°–265° C.

(d) A mixture of 1.90 g (9.7 mmol) of 3,4-dihydro-4-methyl-5H-thieno[3,4-e][1,4]diazepine-2,5(1H)-dione and 15 ml of dimethylformamide is treated under argon with 0.35 g (9.7 mmol) of sodium hydride (60 percent oil dispersion) and stirred for 1 hour. 1.40 ml (9.7 mmol) of diethylchlorophosphate are added dropwise to this solution at −30° C. The mixture is stirred at −20° C. for 10 minutes.

Separately, a solution of 1.08 g (9.7 mmol) of potassium tert.butylate in 3 ml of dimethylformamide is cooled to −50° C. and treated with 1.09 g (9.7 mmol) of ethyl isocyanoacetate. This solution is added dropwise at −10° C. to −20° C. to the mixture obtained according to the preceding paragraph and the resulting mixture is stirred for 0.5 hour. The mixture is neutralised with 1 ml of acetic acid, poured into ca 200 ml of water and extracted three times with chloroform. The combined chloroform phases are washed five times with water, dried over magnesium sulphate and evaporated. After column chromatography of the crude product and recrystallisation from ethyl acetate, there is obtained ethyl 5,6-dihydro-5-methyl-6-oxo-4H-imidazo[1,5-a]thieno[3,4-f][1,4]diazepine-3-carboxylate of melting point 207.5°–208.5° C.

EXAMPLE 42

(a) A solution of 46.7 g (150 mmol) of ethyl (S)-11,12,13,13a-tetrahydro-9-oxo-9H-imidazo[1,5-a]pyrrolo[2,1-c][1,4]benzodiazepine-1-carboxylate in 300 ml of dry tetrahydrofuran is treated dropwise at ca 35° C. with a solution of 8.3 g (377 mmol) of lithium borohydride in 110 ml of dry tetrahydrofuran. The mixture is heated to boiling under reflux for ca 40 hours, cooled to room temperature, treated with 110 ml of 12 percent hydrochloric acid and 20 ml of concentrated hydrochloric acid and again heated to boiling under reflux for 2 hours. After removal of the tetrahydrofuran in vacuo, the residue is made alkaline with concentrated ammonia. The separated material is filtered off under suction and washed with water. After recrystallisation from ethanol, there is obtained (S)-11,12,13,13a-tetrahydro-1-(hydroxymethyl)-9H-imidazo[1,5-a]pyrrolo[2,1-c][1,4]benzodiazepin-9-one of melting point 212°–214° C.

(b) A suspension of 12.1 g (45 mmol) of (S)-11,12,13,13a-tetrahydro-1-(hydroxymethyl)-9H-imidazo[1,5-a]pyrrolo[2,1-c][1,4]benzodiazepin-9-one in 300 ml of methylene chloride is treated with 70 g of manganese dioxide and stirred at room temperature for ca 0.75 hour. After filtration over Dicalit, the filtrate is evaporated in vacuo and the residue is washed with ca 100 ml of boiling ethyl acetate. There is obtained (S)-11,12,13,13a-tetrahydro-9-oxo-9H-imidazo[1,5-a]pyrrolo[2,1-c][1,4]benzodiazepine-1-carboxaldehyde of melting point 206°–208° C.

(c) A suspension of 2.67 g (10 mmol) of (S)-11,12,13,13a-tetrahydro-9-oxo-9H-imidazo[1,5-a]pyrrolo[2,1-c][1,4]benzodiazepine-1-carboxaldehyde and 0.85 g (12.5 mmol) of hydroxylamine hydrochloride in 60 ml of water is treated dropwise at room temperature with a solution of 3.57 g (12.5 mmol) of sodium carbonate decahydrate in 10 ml of water. The mixture is stirred at 70° C. for 4 hours. After cooling, the separated material is filtered off under suction, washed with water and recrystallised directly from 50 ml of dimethylformamide. There is obtained (S)-11,12,13,13a-tetrahydro-9-oxo-9H-imidazo[1,5-a]pyrrolo[2,1-c][1,4]benzodiazepine-1-carboxaldehyde-1-oxime of melting point 285° C.

(d) A solution of 5.24 g (18.5 mmol) of (S)-11,12,13-13a-tetrahydro-9-oxo-9H-imidazo[1,5-a]pyrrolo[2,1-c][1,4]benzodiazepine-1-carboxaldehyde-1-oxime in 50 ml of acetic acid anhydride is heated to boiling under reflux for 3 hours and subsequently evaporated in vacuo. The residue is taken up in chloroform, the solution is washed once with ca 30 ml of saturated sodium hydrogen carbonate solution and once with ca 30 ml of water, dried over magnesium sulphate and evaporated. After column chromatography and recrystallisation from ethyl acetate, there is obtained (S)-11,12,13,13a-tetrahydro-9-oxo-9H-imidazo[1,5-a]pyrrolo[2,1-c][1,4]benzodiazepine-1-carbonitrile of melting point 223°–225° C.

EXAMPLE 43

A mixture of 1.92 g (9 mmol) of (S)-3,11a-dihydro-5H-pyrrolo[2,1-c][1,4]benzodiazepine-5-11(10H)-dione and 15 ml of dimethylformamide is treated with 0.33 g (9 mmol) of sodium hydride (60 percent oil dispersion) and stirred for 0.5 hour. 155 g (9 mmol) of diethylchlorophosphate are added dropwise thereto at −30° C. and the mixture is stirred at −20° C. for 10 minutes.

Separately, a solution of 1 g (9 mmol) of potassium tert.butylate in 3 ml of dimethylformamide is cooled to ca −45° C. and treated with 1.02 g (9 mmol) of ethyl isocyanoacetate. The orange coloured solution obtained is added dropwise at −20° C. to −10° C. to the mixture obtained according to the preceding paragraph and the resulting mixture is stirred without cooling for 0.5 hour. Subsequently, the mixture is neutralised with 1 ml of acetic acid, poured into water and extracted three times with chloroform. The combined chloroform extracts are washed five times with water, dried over magnesium sulphate and evaporated. After chromatography of the crude product and recrystallisation of the resulting material from ethyl acetate/hexane, there is obtained ethyl (R,S)-11,13a-dihydro-9-oxo-9H-imidazo[1,5-a]pyrrolo[2,1-c][1,4]benzodiazepine-1-carboxylate of melting point 184°–185.5° C.

EXAMPLE 44

A mixture of 3.12 g (10 mmol) of ethyl (S)-10,11,12,12a-tetrahydro-8-oxo-8H-imidazo[5,1-c]pyrrolo[1,2-a]thieno[3,2-e][1,4]diazepine-1-carboxylate, 80 mg of powdered potassium cyanide and 30 ml of ethyleneglycol is stirred at 100° C. overnight. After removal of the ethyleneglycol, the residue is purified by column chromatography. There is obtained 2-hydroxyethyl (S)-10,11,12,12a-tetrahydro-8-oxo-8H-imidazo[5,1-c]pyrrolo[1,2-a]thieno[3,2-e][1,4]diazepine-1-carboxylate of melting point 182°–184° C.

EXAMPLE 45

(a) A solution of 2.32 g (10 mmol) of (2R,11aS)-1,2,3,11a-tetrahydro-2-hydroxy-5H-pyrrolo[2,1-c][1,4]benzodiazepine-5,11(10H)-dione in 20 ml of pyridine is treated with 0.86 ml (11 mmol) of methanesulphonyl chloride and stirred at room temperature for 4 hours. After evaporation in vacuo, the residue is treated with water and extracted three times with ca 60 ml of chloroform each time. The combined chloroform extracts are washed twice with ca 30 ml of water each time, dried over magnesium sulphate and evaporated. After recrystallisation from ethanol, there is obtained (2R,11aS)-2,3,5,10,11,11a-hexahydro-5,11-dioxo-1H-pyrrolo[2,1-c][1,4]benzodiazepin-3-yl methanesulphonate of melting point 179°–181° C.

(b) A suspension of 5.92 g (135.7 mmol) of sodium hydride (55 percent oil dispersion) in 150 ml of dry dimethylformamide is treated with 17.0 g (54.8 mmol) of (2R,11aS)-2,3,5,10,11,11a-hexahydro-5,11-dioxo-1H-pyrrolo[2,1-c][1,4]benzodiazepin-3-yl methanesulphonate and stirred at room temperature for ca 16 hours and at 40° C. for ca 16 hours. The mixture is treated with water, poured into ca 300 ml of ice/water, neutralised with glacial acetic acid and left to stand in an ice/bath for 2 hours. The separated material is filtered off under suction, washed with water and recrystallised from dioxan. There is thus obtained (R,S)-1,11a-dihydro-5H- pyrrolo[2,1-c][1,4]benzodiazepine-5,11(10H)-dione of melting point 236°–238° C.

(c) A suspension of 1.01 g (23.2 mmol) of sodium hydride (55 percent oil dispersion) in 35 ml of dry dimethylformamide is treated with 4.15 g (19.4 mmol) of (R,S)-1,11a-dihydro-5H-pyrrolo[2,1-c][1,4]benzodiazepine-5,11(10H)-dione. After completion of the gas evolution, the mixture is cooled to −40° C. and treated dropwise with 3.1 ml (20.2 mmol) of diethylchlorophosphate. After removal of the cooling bath, the mixture is treated dropwise at −20° C. to −15° C. with a solution, cooled in an acetone/dry-ice bath, of 2.33 g (21.3 mmol) of potassium tert.butylate and 2.7 ml (21.3 mmol) of ethyl isocyanoacetate in 8 ml of dry dimethylformamide. When the temperature has reached 20° C., the mixture is neutralised with glacial acetic acid, poured into ca 200 ml of water and left to stand overnight. The separated product is filtered off under suction, washed with water and dried. After recrystallisation from ethyl acetate, there is obtained ethyl (R,S)-13,13a-dihydro-9-oxo-9H-imidazo[1,5-a]pyrrolo[2,1-c][1,4]benzodiazepine-1-carboxylate of melting point 178° C.

EXAMPLE 46

(a) A mixture of 10.0 g of ethyl 5,6-dihydro-5-methyl-6-oxo-4H-imidazo[1,5-a][1,4]benzodiazepine-3-carboxylate, 200 ml of methanol, 0.5 g of ammonium chloride and 30 g of ammonia (100%) is stirred in an autoclave under nitrogen (40 bar) at a temperature of 120° C. for 12 hours. After cooling and discharging the over-pressure, the mixture is evaporated to dryness. After partition of the residue between methylene chloride and water, the organic phase is dried and evaporated. The residue is recrystallised from ethyl acetate, there being obtained 5,6-dihydro-5-methyl-6-oxo-4H-imidazo[1,5-a][1,4]benzodiazepine-3-carboxamide in the form of white crystals of melting point 274°–275° C.

(b) 0.5 g of 5,6-dihydro-5-methyl-6-oxo-4H-imidazo[1,5-a][1,4]benzodiazepine-3-carboxamide is heated to reflux while stirring for 40 hours together with 0.5 g of Sicapent in 150 ml of toluene. The mixture is treated with a 0.5 g portion of Sicapent after 16 hours, 19 hours and 24 hours. The mixture is subsequently cooled and treated with water. The mixture is adjusted to pH 9 with 28 percent sodium hydroxide. After separation of the organic phase, the alkaline-aqueous phase is extracted twice with 250 ml of ethyl acetate each time. The organic extracts are washed twice with saturated sodium chloride solution, dried and evaporated. After crystallisation of the residue from methylene chloride/hexane, there is recovered a portion of unreacted starting material. The mother liquor is evaporated and chromatographed on 100 g of silica gel while eluting with ethyl acetate and alcohol. After recrystallisation of the thus-obtained substance from acetone, there is obtained 5,6-dihydro-5-methyl-6-oxo-4H-imidazo[1,5-a][1,4]benzodiazepine-3-carbonitrile of melting point 184°–185° C.

EXAMPLE 47

(a) A mixture of 12.1 g of 5-(trifluoromethyl)isatin, 50 ml of acetic acid and 50 ml of acetic acid anhydride is treated portionwise at a temperature between 80° C. and 90° C. with 10.0 g of chromium trioxide. 5 minutes after the last addition, the mixture is cooled to room temperature and the separated crystals are filtered off under suction and washed with water. There is thus obtained 5-(trifluoromethyl)isatoic acid anhydride of melting point 264°–266° C.

(b) A suspension of 5.76 g (24.9 mmol) of 5-(trifluoromethyl)isatoic acid anhydride and 2.44 g (27.4 mmol) of sarcosine in 8 ml of dimethyl sulphoxide is stirred at 110° C. for 4 hours, subsequently poured into 70 ml of water and evaporated to dryness in vacuo. After column chromatography on silica gel using ethyl acetate/n-hexane (9:1) for the elution and recrystallization of the product from ethanol, there is obtained 3,4-dihydro-4-methyl-7-(trifluoromethyl)-2H-1,4-benzodiazepine-2,5(1H)-dione of melting point 203°–206° C.

(c) A solution of 2.36 g (9.1 mmol) of 3,4-dihydro-4-methyl-7-(trifluoromethyl)-2H-1,4-benzodiazepine-2,5(1H)-dione in 10 ml of dry dimethylformamide is treated at 5° C. with 1.22 g (10.9 mmol) of potassium tert.butylate and at −40° C. dropwise with 1.4 ml (9.5 mmol) of diethylchlorophosphate.

Separately, a solution of 1.12 g (10 mmol) of potassium tert.butylate in 5 ml of dry dimethylformamide is treated while cooling in an acetone/dry-ice bath with 1.2 ml (10 mmol) of ethyl isocyanoacetate. The thus-obtained orange coloured solution is now added dropwise at −20° C. to −10° C. to the mixture obtained according to the preceding paragraph. The cooling bath is removed, the mixture is neutralized after ca 15 minutes with glacial acetic acid and the resulting mixture is poured into 80 ml of ice/water. The mixture is extracted three times with 60 ml of chloroform each time, the combined chloroform extracts are washed three times with 60 ml of water each time, dried over magnesium sulphate and evaporated. After column chromatography and recrystallisation of the crude product from ethyl acetate, there is obtained ethyl 5,6-dihydro-5-methyl-6-oxo-8-(trifluoromethyl)-4H-imidazo[1,5-a][1,4]benzodiazepine-3-carboxylate of melting point 179°–180° C.

EXAMPLE A

Tablets containing the following ingredients are manufactured:

|  | Per tablet |
|---|---|
| Ethyl (S)-11,12,13,13a-tetrahydro-9-oxo-9H-imidazo[1,5-a]pyrrolo[2,1-c][1,4]-benzodiazepine-1-carboxylate | 10 mg |
| Lactose | 90 mg |
| Maize starch | 29 mg |
| Microcrystalline cellulose | 70 mg |
| Magnesium stearate | 1 mg |
| Total | 200 mg |

EXAMPLE B

Capsules containing the following ingredients are manufactured:

|  | Per capsule |
|---|---|
| Ethyl (S)-11,12,13,13a-tetrahydro-9-oxo-9H-imidazo[1,5-a]pyrrolo[2,1-c][1,4]-benzodiazepine-1-carboxylate | 10 mg |
| Lactose | 165 mg |
| Maize starch | 30 mg |
| Talc | 5 mg |
| Total | 210 mg |

The ethyl (S)-11,12,13,13a-tetrahydro-9-oxo-9H-imidazo[1,5-a]pyrrolo[2,1-c][1,4]benzodiazepine-1-carboxylate, lactose and maize starch are firstly mixed in a mixer and then in a comminuting machine. The mixture is returned to the mixer, the talc is added thereto and the resulting mixture is mixed thoroughly. The mixture is then filled by machine into hard gelatin capsules.

EXAMPLE C

Injection solutions containing the following ingredients are manufactured:

|  | Per ml |
|---|---|
| Ethyl (S)-11,12,13,13a-tetrahydro-9-oxo-9H-imidazo[1,5-a]pyrrolo[2,1-c][1,4]-benzodiazepine-1-carboxylate | 5.0 mg |
| Benzyl alcohol | 0.015 ml |
| Propyleneglycol | 0.4 ml |
| Ethanol (95%) | 0.1 ml |
| Sodium benzoate | 48.8 mg |
| Benzoic acid | 1.2 mg |
| Water for injection q.s. ad | 1.0 ml |

For the manufacture of 10 000 ml of injection solution, 50 g of ethyl (S)-11,12,13,13a-tetrahydro-9-oxo-9H-imidazo[1,5-a]pyrrolo[2,1-c][1,4]benzodiazepine-1-carboxylate are dissolved in 150 ml of benzyl alcohol and 4000 ml of propyleneglycol and 1000 ml of ethanol are added thereto. Then, 12 g of benzoic acid are dissolved in the foregoing mixture and there is added thereto a solution of 488 g of sodium benzoate in 300 ml of water for injection. The solution obtained is made up to a volume of 10 000 ml by the addition of water for injection, filtered and filled into ampoules of suitable size; the residual volume of the ampoules is filled with nitrogen, the ampoules are sealed and sterilised for 30 minutes in an autoclave at 0.7 atmospheres.

EXAMPLE D

Suppositories containing the following ingredients are manufactured:

|  | Per suppository |
|---|---|
| Ethyl (S)-11,12,13,13a-tetrahydro-9-oxo-9H-imidazo[1,5-a]pyrrolo[2,1-c][1,4]-benzodiazepine-1-carboxylate | 0.010 g |
| Cocoa butter (melting point 36°-37° C.) | 1.245 g |
| Carnauba wax | 0.045 g |
| Total | 1.3 g |

The cocoa butter and Carnauba wax are melted in a glass or steel vessel, mixed thoroughly and cooled to 45° C. There is then added the finely powdered ethyl (S)-11,12,13,13a-tetrahydro-9-oxo-9H-imidazo[1,5-a]pyrrolo[2,1-c][1,4]benzodiazepine-1-carboxylate and the mixture is stirred until it is completely dispersed. The mixture is poured into suppository moulds of suitable size and left to cool. The suppositories are then removed from the moulds and packed individually in wax paper or metal foil.

EXAMPLE E

Capsules containing the following ingredients are manufactured:

|  | mg/capsule |
|---|---|
| (+)-5-(o-Chlorophenyl)-1,3-dihydro-3-methyl-7-nitro-2H-1,4-benzodiazepin-2-one | 10.0 |
| Ethyl 8-fluoro-5,6-dihydro-5-methyl-6-oxo-4H-imidazo[1,5-a][1,4]benzodiazepine-3-carboxylate | 100.0 |
| Lactose (crystalline) | 100.0 |
| Maize starch (white) | 27.5 |
| Talc | 10.0 |
| Magnesium stearate | 2.5 |
| Total | 250.0 |

The two active substances are mixed well with the adjuvants and 250.0 mg of the mixture are filled into interlocking capsules of suitable size.

EXAMPLE F

Tablets containing the following ingredients are manufactured:

|  | mg/tablet |
|---|---|
| (+)-5-(o-Chlorophenyl)-1,3-dihydro-3-methyl-7-nitro-2H-1,4-benzodiazepin-2-one | 30.0 |
| Ethyl 8-fluoro-5,6-dihydro-5-methyl-6-oxo-4H-imidazo[1,5-a][1,4]benzodiazepine-3-carboxylate | 30.0 |
| Lactose (powdered) | 15.0 |
| Maize starch (white) | 19.5 |
| Povidon K30 | 3.5 |
| Maize starch (white) | 10.0 |
| Magnesium stearate | 2.0 |
| Total | 110.0 |

The two active substances, powdered lactose and the first portion of white maize starch are mixed and sieved. This mixture is moistened with a solution of the Povidon K30 in water, kneaded, granulated, dried and sieved. The second portion of white maize starch and the magnesium stearate are added to the granulate. After mixing, the mass obtained is pressed to tablets weighing 110 mg.

EXAMPLE G

Tablets containing the following ingredients are manufactured:

|  | mg/tablet |
|---|---|
| (+)-5-(o-Chlorophenyl)-1,3-dihydro-3-methyl-7-nitro-2H-1,4-benzodiazepin-2-one | 30 |
| Ethyl 8-fluoro-5,6-dihydro-5-methyl-6-oxo-4H-imidazo[1,5-a][1,4]benzodiazepine-3-carboxylate | 100 |
| Lactose (powdered) | 22 |
| Maize starch (white) | 22 |
| Povidon K30 | 6 |
| Maize starch (white) | 16 |
| Magnesium stearate | 4 |
| Total | 200 |

The two active substances, powdered lactose and the first portion of white maize starch are mixed and sieved. This mixture is moistened with a solution of the Providon K30 in water, kneaded, granulated, dried and sieved. The second portion of white maize starch and the magnesium stearate are added to the granulate. After mixing, the mass obtained is pressed to tablets weighing 200 mg.

What is claimed:

1. A process for the manufacture of compounds of the formula

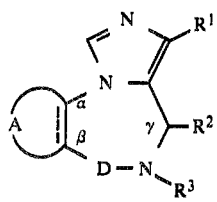

wherein A together with the two carbon atoms denoted as α and β is selected from the group consisting of

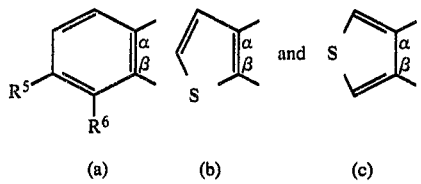

(a)    (b)    (c)

the dotted line represents the double bond present in groups (a) and (b), D is C=O or C=S, $R^1$ is selected from the group consisting of cyano, lower alkanoyl and a group of the formula —COOR$^4$, $R^4$ is selected from the group consisting of methyl, ethyl, isopropyl and 2-hydroxyethyl, $R^5$ is selected from the group consisting of hydrogen, trifluoromethyl and halogen and $R^6$ is selected from the group consisting of hydrogen, trifluoromethyl, halogen and lower alkyl and either $R^2$ is hydrogen and $R^3$ is hydrogen or lower alkyl or $R^2$ and $R^3$ together are trimethylene or propenylene and the carbon atom denoted as γ has the S- or R,S-configuration, which comprises
reacting a compound of the formula

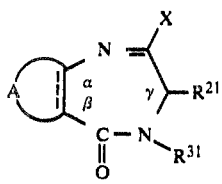

wherein A and the dotted line are as above, X represents a leaving group, and either $R^{21}$ is hydrogen and $R^{31}$ is lower alkyl, or $R^{21}$ and $R^{31}$ together are trimethylene or propenylene and the carbon atom denoted as has the S- or R,S-configuration, in the presence of a base with an isocyanoacetic ester of the formula

CN—CH$_2$—COOR$^{41}$ wherein $R^{41}$ is methyl, ethyl or isopropyl.

* * * * *